US008691547B2

(12) United States Patent
Omura et al.

(10) Patent No.: US 8,691,547 B2
(45) Date of Patent: *Apr. 8, 2014

(54) COENZYME-LINKED GLUCOSE DEHYDROGENASE AND POLYNUCLEOTIDE ENCODING THE SAME

(75) Inventors: Hironori Omura, Fukuyama (JP); Hirokazu Sanada, Mihara (JP); Takako Yada, Fukuyama (JP); Ayaka Atsumi, Tsukuba (JP); Tetsunari Morita, Fukuyama (JP); Emi Ishimaru, Fukuyama (JP)

(73) Assignee: Ikeda Food Research Co., Ltd., Fukuyama (JP)

( * ) Notice: Subject to any disclaimer, the term of this patent is extended or adjusted under 35 U.S.C. 154(b) by 1371 days.

This patent is subject to a terminal disclaimer.

(21) Appl. No.: 11/886,885

(22) PCT Filed: Mar. 27, 2006

(86) PCT No.: PCT/JP2006/306198
§ 371 (c)(1),
(2), (4) Date: Apr. 1, 2008

(87) PCT Pub. No.: WO2006/101239
PCT Pub. Date: Sep. 28, 2006

(65) Prior Publication Data
US 2012/0122130 A1    May 17, 2012

(30) Foreign Application Priority Data
Mar. 25, 2005   (JP) ................. 2005-089884

(51) Int. Cl.
*C12N 9/04*     (2006.01)
*C12N 9/02*     (2006.01)
*C12N 9/96*     (2006.01)
*C12N 1/20*     (2006.01)
*C12N 1/00*     (2006.01)
*C12N 15/00*    (2006.01)
*C12Q 1/54*     (2006.01)
*C07H 21/04*    (2006.01)

(52) U.S. Cl.
USPC ............. 435/190; 435/14; 435/189; 435/188; 435/252.3; 435/252.33; 435/254.11; 435/254.2; 435/320.1; 536/23.2

(58) Field of Classification Search
None
See application file for complete search history.

(56) References Cited

U.S. PATENT DOCUMENTS

| | | |
|---|---|---|
| 5,286,362 A | 2/1994 | Hoenes et al. |
| 6,100,037 A | 8/2000 | Phillips et al. |
| 6,103,509 A | 8/2000 | Sode et al. |
| 6,338,790 B1 | 1/2002 | Feldman et al. |
| 6,558,920 B1 | 5/2003 | Hata et al. |
| 6,773,564 B1 | 8/2004 | Yugawa et al. |
| 7,049,114 B1 | 5/2006 | Sode et al. |
| 7,067,295 B1 | 6/2006 | Sode et al. |
| 7,132,270 B2 | 11/2006 | Kratzsch et al. |
| 7,244,600 B2 | 7/2007 | Sode et al. |
| 2003/0082595 A1 | 5/2003 | Jiang et al. |
| 2006/0063217 A1 | 3/2006 | Omura et al. |
| 2007/0105173 A1 | 5/2007 | Takeshima et al. |

FOREIGN PATENT DOCUMENTS

| | | |
|---|---|---|
| EP | 0 094 161 A1 | 11/1983 |
| EP | 0 992 589 A2 | 4/2000 |
| EP | 1 584 675 A1 | 10/2005 |
| JP | 59-025700 A | 2/1984 |
| JP | 10-239273 | 9/1998 |
| JP | 10-243786 A | 9/1998 |
| JP | 2000-312588 A | 11/2000 |
| JP | 2000-350588 A | 12/2000 |
| JP | 2000-354495 A | 12/2000 |
| JP | 2001-037483 A | 2/2001 |
| JP | 2001-046078 A | 2/2001 |
| JP | 2001-197888 A | 7/2001 |
| JP | 2001-346587 A | 12/2001 |
| JP | 2002-223772 A | 8/2002 |
| JP | 2002-526759 A | 8/2002 |
| JP | 2004-512047 A | 4/2004 |
| JP | 2004-173538 A | 6/2004 |
| JP | 2004-313172 A | 11/2004 |
| JP | 2004-313180 A | 11/2004 |
| JP | 2004-344145 A | 12/2004 |
| JP | 2008-206433 A * | 9/2008 |
| WO | WO-98/20136 A1 | 5/1998 |

(Continued)

OTHER PUBLICATIONS

Machida et al. Genome sequencing and analysis of *Aspergillus oryzae*, Nature (Dec. 2005), 438: 1157-1161.*
Kataoka et al. *Escherichia* cli transformant expressing the glucose dehydrogenase gene from *Bacillus megaterium* as a cofactor regenerator in a chiral alcohol production system, Biosci Biotechnol Biochem (1998), 62: 167-169.*
UniProt Accession No. G8E4B4, Glucose dehydrogenase, created Jan. 25, 2012.*
Bak, T G; "Studies on Glucose Dehydrogenase of *Aspergillus olyzae* III. General Enzymatic Properties"; Biochim. Biophys. Acta, vol. 146, No. 2, Jan. 1, 1967, pp. 317-327.

(Continued)

*Primary Examiner* — Iqbal H Chowdhury
(74) *Attorney, Agent, or Firm* — Finnegan, Henderson, Farabow, Garrett & Dunner, LLP

(57) ABSTRACT

The present invention provides members that produce on a large scale a coenzyme-linked glucose dehydrogenase which has excellent substrate-recognizing ability toward glucose while providing low action on maltose. The present invention relates to a polynucleotide encoding a soluble coenzyme-linked glucose dehydrogenase that catalyzes the oxidation of glucose in the presence of an electron acceptor and has an activity toward maltose of 5% or lower; a polypeptide encoded by the nucleotide sequence of the polynucleotide; a recombinant vector carrying the polynucleotide; a transformed cell produced using the recombinant vector; a method for producing a polypeptide comprising culturing the transformed cell and collecting from the cultivated products a polypeptide that links to FAD to exert the glucose dehydration activity; a method for determination of glucose using the polypeptide; a reagent composition for determination of glucose; and a biosensor.

17 Claims, 6 Drawing Sheets

(56) References Cited

FOREIGN PATENT DOCUMENTS

| WO | WO-02/072839 A1 | 9/2002 |
| WO | WO-03/012071 A2 | 2/2003 |
| WO | WO-2004/058958 A1 | 7/2004 |
| WO | WO-2004/058958 A1 | 7/2004 |

OTHER PUBLICATIONS

Yoshida, H. et al.; "Construction of multi-chimeric pyrroloquinoline quinone glucose dehydrogenase with improved enzymatic properties and application in glucose monitoring"; Biotechnology Letters, vol. 22, No. 18, Sep. 1, 2000, pp. 1505-1510.

Notice of Submission of Published Documents issued on Feb. 10, 2009 for counterpart Japanese Patent Application No. 2007-509374.

Bak T G et al.; "Studies on glucose dehydrogenase of *Aspergillus oryzae*"; Biochimica Et Biophysica Acta, vol. 146, (1967), pp. 328-335.

Tsujimura, Selya et al.; "Absolute quantification of glucose by coulometry using novel glucose dehydrogenase"; Abstract of the 72nd Meeting of the Electrochemical Society of Japan, 2D04, 2005.

European Search Report issued for corresponding application No. EP 11156659.2, dated Jun. 28, 2011.

European Search Report issued for corresponding application No. EP 11156661.8, dated Jun. 6, 2011.

European Search Report issued for corresponding application No. EP 11156657.6, dated Aug. 25, 2011.

European Search Report issued for corresponding application No. EP 11156649.3, dated Sep. 23, 2011.

European Search Report issued for corresponding application No. EP 11156664.2, dated Sep. 23, 2011.

Summary of the Annual Meeting of Japan Society for Bioscience 2004, Biotechnology and Agrochemistry, Mar. 5, 2004, 96, 2A25p11.

New Biochemical Experiment Course 1 Protein II "Primary Structure", Tokyo Kagaku Dojin, Dec. 1, 1993, $1^{st}$ edition, $2^{nd}$ printing, pp. 1-24.

Office Action issued on Aug. 2, 2011 in connection with corresponding to Japanese Patent Application No. JP 2007-509374, English language translation attached.

Isao Ishida and Tamie Ando (ed.), "Laboratory Manual for Gene Expression, Production of useful protein in high expression system", Kodansha Scientific Ltd., pp. 100-129 (1994). (Partial English translations).

Hiroya Yurimoto and Yasuyoshi Sakai, "Heterologous gene expression system by methanol-utilizing yeast", Chemistry & Biology, 38(8):533-540 (2000). (Partial English translations).

Kojima, S. et al.; "Fundamental study for an oxygen-insensitive amperometric glucose sensor using a novel glucose dehydrogenase"; Chemical Sensors, vol. 20, Supplement B, Jul. 11, 2004, pp. 768-769.

Kojima, N. et al.; "Shinki Glucose Dehydrogenase o Mochiita Sanso Fukan' no-sei Ketto Sensor no Kiso Kento (1)"; The Japan Society for Analytical Chemistry Nenkai Koen Yoshishu, vol. 53, Aug. 18, 2004, p. 80.

Inose, K. et al.; "Cloning and expression of the gene encoding catalytic subunit of thermostable glucose dehydrogenase from *Burkholderia cepacia* in *Escherichia coli*"; Biochimica ct Biophysica Acta, vol. 1645, No. 2, Feb. 21, 2003, pp. 133 to 138.

Soda, K. et al.; "A novel thermostable glucose dehydrogenase varying temperature properties by altering its quaternary structures"; Enzyme and Microbial Technology, vol. 19, 1996, pp. 82-85.

Iwashita, K. et al.; "Purification and Characterization of Extracellular and Cell Wall Bound β-Glucosidases from *Aspergillus kawachii*"; Biosci. Biotechnol. Biochem., vol. 62, No. 10, 1998, pp. 1938-1946.

Tsujimura, S. et al.; "Novel FAD-Dependent Glucose Dehydrogenase for a Dioxygen-Insensitive Glucose Biosensor"; Biosci. Biotechnol. Biochem., vol. 70, No. 3, 2006, pp. 654-659.

Hayano, K. et al.; "Purificatioin and Properties of 3-Ketosucrose-forming Enzyme from the Cells of *Agrobacterium tumefaciens*"; The Journal of Biological Chemistry, vol. 242, No. 16, Issue of Aug. 25, pp. 3665-3672, 1967.

Pharmaceutical and Food Safety Bureau Issue No. 0207005, Feb. 7, 2005; "Safety Measures of Simple Instrument for Self-Checking Blood Glucose and Glucose Kit for Self-Testing Blood Glucose (Using Pyrrolo-Quinoline Quinone As Coenzyme in Glucose Dehydrogenase Method)".

Tsugawa, W. et al.; "Purification of a Marine Bacterial Glucose Dehydrogenase from *Cytophaga marinoflava* and its Application for Measurement of 1,5-Anhydro-D-Glucitol"; Applied Biochemistry and Biotechnology, vol. 56, pp. 301-310, 1996.

Tsugawa, W. et al.; "Fluorescent measurement of 1,5-anhydro-D-glucitol based on a novel marine bacterial glucose dehydrogenase"; Enzyme and Microbial Technology 22; pp. 269-274, 1998.

Vole, J. et al.; "Pyranose 2-dehydrogenase, a novel sugar oxidoreductase from the basidiomycete fungus *Agaricus bisporus*"; Arch Microbiol (1997) 167; pp. 119-125.

Morrison, S.C. et al.; "Characterization of a glucose 3-dehydrogenase from the cultivated mushroom (*Agaricus bisporus*)"; Appl. Microbiol Biotechnol (1999) 51; pp. 58-64.

Vole, J. et al.; "Screening of basidiomycete fungi for the quinone-dependent sugar C-2/C-3 oxidoreductase, pyranose dehydrogenase, and properties of the enzyme from *Macrolepiota rhacodes*"; Arch Microbiol (2001) 176; pp. 178-186.

Society for Biotechnology, Japan (Oct. 28-30, 2002). (English translation attached).

Bak, T.; "Studies on Glucose Dehydrogenase of *Aspergillus oryzae* II, Purification and Physical and Chemical Properties"; Biochim. Biophys. Acta, 139 (1967), pp. 277-293.

Witt, S. et al.; "Structural and Kinetic Properties of Nonglycosylated Recombinant *Penicillium amagasakiense* Glucose Oxidase Expressed in *Escherichia coli*"; Applied and Environmental Microbiology, vol. 64, No. 4, Apr. 1998, pp. 1405-1411.

Cavener, D. et al.; "Biphasic expression and function of glucose dehydrogenase in *Drosophila melanogaster*"; Proc. Natl. Acad. Sci., vol. 80, Oct. 1983, pp. 6286-6288.

Harper's Review of Biochemistry, $20^{th}$ ed., by Martin et al., 1985, p. 503; an English translation thereof.

Communication pursuant to Rule 114(2) EPC issued Aug. 26, 2010 by the European Patent Office in connection with European Patent Application No. 06730146.5.

Rolke et al., "Functional analysis of $H_2O_2$-generating systems in *Botrytis cinerea*: the major Cu-Zn-superoxide dismutase (BC50D1) contributes to virulence on French bean, whereas a glucose oxidase (BCGOD1) is dispensable," *Molecular Plant Pathology*, 5(1): 17-27 (2004).

* cited by examiner

FIG. 1

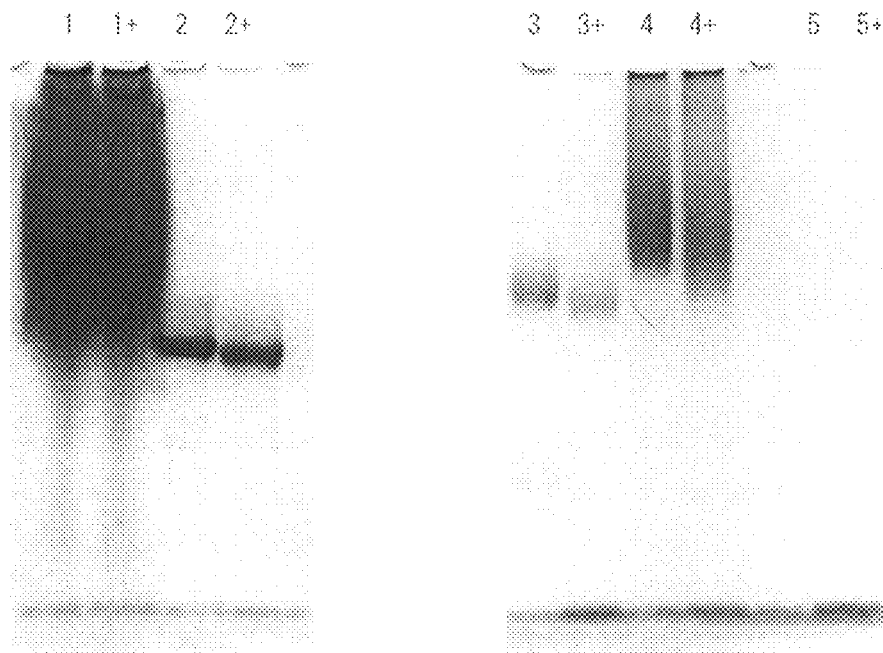

LANE NO. AND SAMPLE NAME
1: PURIFIED ENZYME 1 (DERIVED FROM LIQUID-CULTIVATED WILD STRAIN
   (A. terreus)).
2: PURIFIED ENZYME 2 (DERIVED FROM BRAN-CULTIVATED WILD STRAIN
   (A. terreus)).
3: PURIFIED ENZYME 5 (DERIVED FROM RECOMBINANT MOLD
   (A. oryzae)).
4: PURIFIED ENZYME 6 (DERIVED FROM RECOMBINANT YEAST
   (Candida boidinni)).
5: PURIFIED ENZYME 4 (DERIVED FROM RECOMBINANT E. COLI).
   (IN LANES INDICATED WITH (+),
   EACH SAMPLE SUBJECTED TO GLYCOPEPTIDASE TREATMENT WAS LOADED).

FIG. 2

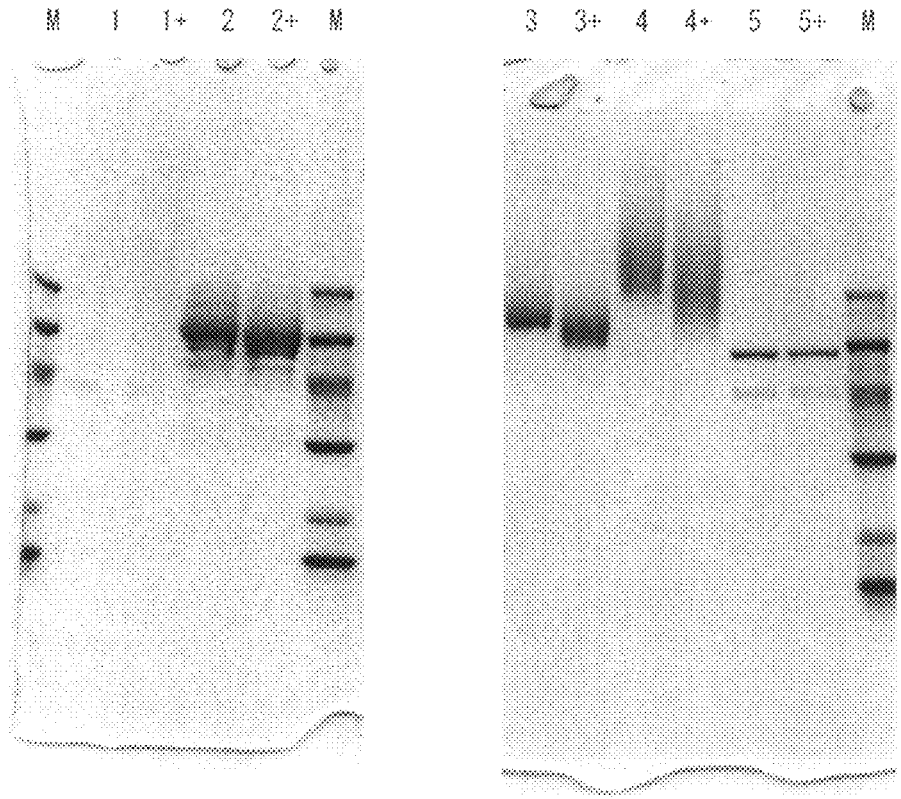

LANE NO. AND SAMPLE NAME

1: PURIFIED ENZYME 1 (DERIVED FROM LIQUID-CULTIVATED WILD STRAIN (A. terreus)).
2: PURIFIED ENZYME 2 (DERIVED FROM BRAN-CULTIVATED WILD STRAIN (A. terreus)).
3: PURIFIED ENZYME 5 (DERIVED FROM RECOMBINANT MOLD (A. oryzae)).
4: PURIFIED ENZYME 6 (DERIVED FROM RECOMBINANT YEAST (Candida boidinni)).
5: PURIFIED ENZYME 4 (DERIVED FROM RECOMBINANT E. COLI).
(IN LANES INDICATED WITH (+),
EACH SAMPLE SUBJECTED TO GLYCOPEPTIDASE TREATMENT WAS LOADED).
M: LMW MARKER (MANUFACTURED BY AMERSHAM PHARMACIA BIOTECH, INC.)

E. COLI: PURIFIED ENZYME 4 DERIVED FROM RECOMBINANT
    E. COLI WAS USED.

MOLD: PURIFIED ENZYME 5 DERIVED FROM RECOMBINANT MOLD
    (A. oryzae) WAS USED.

YEAST: PURIFIED ENZYME 6 DERIVED FROM RECOMBINANT YEAST
    (Candida Boidinni) WAS USED.

E. COLI: PURIFIED ENZYME 4 DERIVED FROM RECOMBINANT
E. COLI WAS USED.
MOLD: PURIFIED ENZYME 5 DERIVED FROM RECOMBINANT MOLD
(A. oryzae) WAS USED.
WILD: PURIFIED ENZYME 1 DERIVED FROM WILD STRAIN
(A. terreus) WAS USED.
YEAST: PURIFIED ENZYME 6 DERIVED FROM RECOMBINANT YEAST
(Candida Boidinni) WAS USED.

SEQUENCE LISTING

```
<160> NUMBER OF SEQ ID NOS: 14

<210> SEQ ID NO 1
<211> LENGTH: 1779
<212> TYPE: DNA
<213> ORGANISM: Aspergillus terreus

<400> SEQUENCE: 1
atgttgggaa agctctcctt cctcagtgcc ctgtccctgg cagtggcggc acctttgtcc      60
aactccacgt ccgccaaata tgattatatc gttattggag gcggtactag cggtttggcc     120
gtcgcaaacc gtctatcgga ggatccaaac gtgaacgtac tcattctgga ggccggtggc     180
tcggtctgga acaatcccaa tgtcacaaac gtggatggct acgggcttgc ttttgggtct     240
gacattgact ggcaatacca gtccgtcaac cagccatatg gaggcaacct tagtcaagtg     300
cttcgtgccg gcaaggccct tggtggtact agtactatca atggcatggc ctatacgcgc     360
gccgaggatg tccagatcga cgcctgggaa accattggca acacaggatg gacgtggaag     420
aatctgttcc cttactatcg gaagagcgag aactttactg tccctaccaa atcgcagacc     480
tctcttggag cgtcgtatga agctggagcc cacgccacg agggtcccct tgacgttgcc      540
ttcactcaga tcgagtcgaa caacctgacc acttacctca accgtacctt ccagggcatg     600
ggactcccat ggacggagga cgtcaatggc ggaaagatgc gcggctttaa cttataccc      660 tccaccgtga atcttgagga gtatgtgcgc gaagacgccg ctcgtgcata ctactggccc     720
tacaagtccc gtcccaactt gcatgtcctg ctcaacactt tgccaaccg gattgtgtgg      780 gacggcgaag cccatgacgg ccacatcact gccagtggtg tcgagatcac ttccaggaac     840
ggcactgttc gtgttatcaa tgcggagaag gaagtcattg tctctgccgg tgccttgaag     900
tccccggcta tccttgaact ttctggaatt ggcaaccct gcgttcttga caagcacaac      960
atccccgtca aggtcaacct cccgactgtc ggcgagaacc ttcaggacca agtgaacagc    1020
cacatggatg catcgggcaa cacttccatc tctggaacca aggcagtctc ctacccgat    1080 gtctatacg tcttcggtga cgaagccgag tcggtcgcca aacagatccg tgccaacctg    1140
aagcaatacg ccgccgacac cgccaaggcc aacgaaaca ttatgaaggc cgccgatctg    1200
gagcgtctct tcgaggtcca gtatgacctt atttttcaagg gcagagttcc aatcgctgaa    1260
gtcctgaact atccgggcag cgccgacgtcc gtgtttgcag aattctgggc cctccttccc    1320
ttcgctcgtg gaagtgttca catcggttct tcaaacccgg ccgagttccc tgtcatcaac    1380
cccaactatt tcatgctcga ctgggacgcg aagagctacg ttgccgttgc gaagtatatc    1440
cgccgttcgt tcgagagcta ccctctcagc agtatcgtga aggagtctac ccctggctat    1500
gatgttatcc cccggaacgc ttctgagcag agctggaaag aatgggtctt tgataagaac    1560
tatcgttcta acttccatcc cgtcggcacg gctgccatga tgcctcgtga gattggtggt    1620
gtcgtggacg agcgtctgaa tgtctatggc actacgaatg tcagagttgt agatgcttcg    1680
gtccttccat tccaggtctg cggccatttg gtgagcacac tatacgctgt ggccgaacgg    1740
```
gcggcggatc tcatcaaggc cgatgctggt cgtcgttag          1779

<210> SEQ ID NO 2
<211> LENGTH: 592
<212> TYPE: PRT
<213> ORGANISM: Aspergillus terreus

<400> SEQUENCE: 2

Met Leu Gly Lys Leu Ser Phe Leu Ser Ala Leu Ser Leu Ala Val Ala
1               5                   10                  15

Ala Pro Leu Ser Asn Ser Thr Ser Ala Lys Tyr Asp Tyr Ile Val Ile
            20                  25                  30

Gly Gly Gly Thr Ser Gly Leu Ala Val Ala Asn Arg Leu Ser Glu Asp
        35                  40                  45

Pro Asn Val Asn Val Leu Ile Leu Glu Ala Gly Gly Ser Val Trp Asn
    50                  55                  60

Asn Pro Asn Val Thr Asn Val Asp Gly Tyr Gly Leu Ala Phe Gly Ser
65                  70                  75                  80

Asp Ile Asp Trp Gln Tyr Gln Ser Val Asn Gln Pro Tyr Gly Gly Asn
                85                  90                  95

Leu Ser Gln Val Leu Arg Ala Gly Lys Ala Leu Gly Gly Thr Ser Thr
            100                 105                 110

Ile Asn Gly Met Ala Tyr Thr Arg Ala Glu Asp Val Gln Ile Asp Ala
        115                 120                 125

Trp Glu Thr Ile Gly Asn Thr Gly Trp Thr Trp Lys Asn Leu Phe Pro
130                 135                 140

Tyr Tyr Arg Lys Ser Glu Asn Phe Thr Val Pro Thr Lys Ser Gln Thr
145                 150                 155                 160

Ser Leu Gly Ala Ser Tyr Glu Ala Gly Ala His Gly His Glu Gly Pro
                165                 170                 175

Leu Asp Val Ala Phe Thr Gln Ile Glu Ser Asn Asn Leu Thr Thr Tyr
            180                 185                 190

Leu Asn Arg Thr Phe Gln Gly Met Gly Leu Pro Trp Thr Glu Asp Val
        195                 200                 205

Asn Gly Gly Lys Met Arg Gly Phe Asn Leu Tyr Pro Ser Thr Val Asn
    210                 215                 220

Leu Glu Glu Tyr Val Arg Glu Asp Ala Ala Arg Ala Tyr Tyr Trp Pro
225                 230                 235                 240

Tyr Lys Ser Arg Pro Asn Leu His Val Leu Leu Asn Thr Phe Ala Asn
                245                 250                 255

Arg Ile Val Trp Asp Gly Glu Ala His Asp Gly His Ile Thr Ala Ser
            260                 265                 270

Gly Val Glu Ile Thr Ser Arg Asn Gly Thr Val Arg Val Ile Asn Ala
        275                 280                 285

Glu Lys Glu Val Ile Val Ser Ala Gly Ala Leu Lys Ser Pro Ala Ile
    290                 295                 300

Leu Glu Leu Ser Gly Ile Gly Asn Pro Ser Val Leu Asp Lys His Asn
305                 310                 315                 320

Ile Pro Val Lys Val Asn Leu Pro Thr Val Gly Glu Asn Leu Gln Asp
                325                 330                 335

Gln Val Asn Ser His Met Asp Ala Ser Gly Asn Thr Ser Ile Ser Gly
            340                 345                 350

Thr Lys Ala Val Ser Tyr Pro Asp Val Tyr Asp Val Phe Gly Asp Glu
        355                 360                 365

Ala Glu Ser Val Ala Lys Gln Ile Arg Ala Asn Leu Lys Gln Tyr Ala
    370                 375                 380

Ala Asp Thr Ala Lys Ala Asn Gly Asn Ile Met Lys Ala Ala Asp Leu
385                 390                 395                 400

Glu Arg Leu Phe Glu Val Gln Tyr Asp Leu Ile Phe Lys Gly Arg Val
                405                 410                 415

Pro Ile Ala Glu Val Leu Asn Tyr Pro Gly Ser Ala Thr Ser Val Phe
            420                 425                 430

Ala Glu Phe Trp Ala Leu Leu Pro Phe Ala Arg Gly Ser Val His Ile
        435                 440                 445

Gly Ser Ser Asn Pro Ala Glu Phe Pro Val Ile Asn Pro Asn Tyr Phe
    450                 455                 460

Met Leu Asp Trp Asp Ala Lys Ser Tyr Val Ala Val Ala Lys Tyr Ile
465                 470                 475                 480

Arg Arg Ser Phe Glu Ser Tyr Pro Leu Ser Ser Ile Val Lys Glu Ser
                485                 490                 495

Thr Pro Gly Tyr Asp Val Ile Pro Arg Asn Ala Ser Glu Gln Ser Trp
            500                 505                 510

Lys Glu Trp Val Phe Asp Lys Asn Tyr Arg Ser Asn Phe His Pro Val
        515                 520                 525

Gly Thr Ala Ala Met Met Pro Arg Glu Ile Gly Gly Val Val Asp Glu
    530                 535                 540

Arg Leu Asn Val Tyr Gly Thr Thr Asn Val Arg Val Val Asp Ala Ser
545                 550                 555                 560

Val Leu Pro Phe Gln Val Cys Gly His Leu Val Ser Thr Leu Tyr Ala
                565                 570                 575

Val Ala Glu Arg Ala Ala Asp Leu Ile Lys Ala Asp Ala Gly Arg Arg
            580                 585                 590

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgtcatggta cctccaactc cacgtccgcc aa                              32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agtgtactgc agctaacgac gaccagcatc gg                              32

<210> SEQ ID NO 5
<211> LENGTH: 214
<212> TYPE: DNA
<213> ORGANISM: Aspergillus terreus
<220> FEATURE:
<221> NAME/KEY: modified_base
<222> LOCATION: (14)..(14)
<223> OTHER INFORMATION: a, c, t or g
<220> FEATURE:
<221> NAME/KEY: modified_base
<222> LOCATION: (17)..(17)

```
<223> OTHER INFORMATION: a, c, t or g
<220> FEATURE:
<221> NAME/KEY: modified_base
<222> LOCATION: (20)..(20)
<223> OTHER INFORMATION: a, c, t or g
<220> FEATURE:
<221> NAME/KEY: modified_base
<222> LOCATION: (41)..(41)
<223> OTHER INFORMATION: a, c, t or g
<220> FEATURE:
<221> NAME/KEY: modified_base
<222> LOCATION: (47)..(47)
<223> OTHER INFORMATION: a, c, t or g
<220> FEATURE:
<221> NAME/KEY: modified_base
<222> LOCATION: (62)..(62)
<223> OTHER INFORMATION: a, c, t or g
<220> FEATURE:
<221> NAME/KEY: modified_base
<222> LOCATION: (65)..(65)
<223> OTHER INFORMATION: a, c, t or g
<220> FEATURE:
<221> NAME/KEY: modified_base
<222> LOCATION: (137)..(137)
<223> OTHER INFORMATION: a, c, t or g
<220> FEATURE:
<221> NAME/KEY: modified_base
<222> LOCATION: (161)..(161)
<223> OTHER INFORMATION: a, c, t or g
<220> FEATURE:
<221> NAME/KEY: modified_base
<222> LOCATION: (170)..(170)
<223> OTHER INFORMATION: a, c, t or g

<400> SEQUENCE: 5
tbgargcmgg hgvntcngbn ydsaacaayy ysraygtvwc naaysyndhb ggytayrgvh      60
yngcnttygg vwcbsmbrty gaytggsmvt aymarwcbrw baaccarmvv taygsaggmr     120
rymwdmvbca rrybhtncgw gcbgghaarg yymtbggwgg nacbagyacn atcaatggma     180
tgkcmtayac bcgvgcmsar gaygtbcara tyga                                214

<210> SEQ ID NO 6
<211> LENGTH: 88
<212> TYPE: DNA
<213> ORGANISM: Aspergillus terreus
<220> FEATURE:
<221> NAME/KEY: modified_base
<222> LOCATION: (71)..(71)
<223> OTHER INFORMATION: a, c, t or g

<400> SEQUENCE: 6
tyctygarct ktchgghrtk ggmaacccdd ssvtyytbra mraghacaay atmhcmsymv      60
ddgtyraymt nmcvacygty ggvgaraa                                        88

<210> SEQ ID NO 7
<211> LENGTH: 209
<212> TYPE: DNA
<213> ORGANISM: Aspergillus terreus
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (87)..(87)
<223> OTHER INFORMATION: a, c, t or g

<400> SEQUENCE: 7
atcaayccha actaytwyat gytygrnyrr gayrbbrmrd shyavryyrs bryhgcsmar      60
twyatymgsh vbdybytbsr baaykmnccw ytbwvcdvwh tyrtkrvvdm kkmdryyhmb     120
```

```
ssykrhbwbd hyrhvvyhys drmyrvtkch dmsvrbdvsd vdwrrdhhdr dkksbtyrad      180
rmdrmytayc gwwchaactw ccayccmgt                                       209
```

<210> SEQ ID NO 8  
<211> LENGTH: 15  
<212> TYPE: PRT  
<213> ORGANISM: Aspergillus terreus  
<220> FEATURE:  
<221> NAME/KEY: MOD_RES  
<222> LOCATION: (2)..(2)  
<223> OTHER INFORMATION: Ala or Gly  
<220> FEATURE:  
<221> NAME/KEY: MOD_RES  
<222> LOCATION: (8)..(8)  
<223> OTHER INFORMATION: Ala or Val  
<220> FEATURE:  
<221> NAME/KEY: MOD_RES  
<222> LOCATION: (9)..(9)  
<223> OTHER INFORMATION: Ile or Val

<400> SEQUENCE: 8

```
Gly Xaa Gly Thr Ser Gly Leu Xaa Xaa Ala Asn Arg Leu Ser Glu
1               5                   10                  15
```

<210> SEQ ID NO 9  
<211> LENGTH: 26  
<212> TYPE: PRT  
<213> ORGANISM: Aspergillus terreus  
<220> FEATURE:  
<221> NAME/KEY: MOD_RES  
<222> LOCATION: (5)..(5)  
<223> OTHER INFORMATION: Ala or Val  
<220> FEATURE:  
<221> NAME/KEY: MOD_RES  
<222> LOCATION: (6)..(6)  
<223> OTHER INFORMATION: Ile or Leu  
<220> FEATURE:  
<221> NAME/KEY: MOD_RES  
<222> LOCATION: (16)..(16)  
<223> OTHER INFORMATION: Ala or Ser  
<220> FEATURE:  
<221> NAME/KEY: MOD_RES  
<222> LOCATION: (21)..(21)  
<223> OTHER INFORMATION: Glu or Gln

<400> SEQUENCE: 9

```
Arg Ala Gly Lys Xaa Xaa Gly Gly Thr Ser Thr Ile Asn Gly Met Xaa
1               5                   10                  15

Tyr Thr Arg Ala Xaa Asp Val Gln Ile Asp
                20                  25
```

<210> SEQ ID NO 10  
<211> LENGTH: 13  
<212> TYPE: PRT  
<213> ORGANISM: Aspergillus terreus  
<220> FEATURE:  
<221> NAME/KEY: MOD_RES  
<222> LOCATION: (3)..(3)  
<223> OTHER INFORMATION: Ala or Leu  
<220> FEATURE:  
<221> NAME/KEY: MOD_RES  
<222> LOCATION: (4)..(4)  
<223> OTHER INFORMATION: Ile or Leu  
<220> FEATURE:  
<221> NAME/KEY: MOD_RES  
<222> LOCATION: (10)..(10)  
<223> OTHER INFORMATION: Ile or Val

<400> SEQUENCE: 10

```
Ser Pro Xaa Xaa Leu Glu Leu Ser Gly Xaa Gly Asn Pro
1               5                   10
```

```
<210> SEQ ID NO 11
<211> LENGTH: 7
<212> TYPE: PRT
<213> ORGANISM: Aspergillus terreus

<400> SEQUENCE: 11

Thr Val Gly Glu Asn Leu Gln
1               5

<210> SEQ ID NO 12
<211> LENGTH: 11
<212> TYPE: PRT
<213> ORGANISM: Aspergillus terreus
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (8)..(8)
<223> OTHER INFORMATION: Asn or Ser
<220> FEATURE:
<221> NAME/KEY: MOD_RES
<222> LOCATION: (9)..(9)
<223> OTHER INFORMATION: Ile or Val

<400> SEQUENCE: 12

Leu Leu Pro Phe Xaa Arg Gly Xaa Xaa His Ile
1               5                   10

<210> SEQ ID NO 13
<211> LENGTH: 19
<212> TYPE: DNA
<213> ORGANISM: Aspergillus terreus

<400> SEQUENCE: 13
ttggwggygg wacyagtgg                                                19

<210> SEQ ID NO 14
<211> LENGTH: 20
<212> TYPE: DNA
<213> ORGANISM: Aspergillus terreus

<400> SEQUENCE: 14
gtkcckacgg gatggaagtt                                               20
```

COENZYME-LINKED GLUCOSE DEHYDROGENASE AND POLYNUCLEOTIDE ENCODING THE SAME

TECHNICAL FIELD

The present invention relates to a novel coenzyme-linked glucose dehydrogenase (hereinafter, may be referred to as "GLD"), a polynucleotide encoding the same, a method for producing the same, a method for producing the GLD, and use of the GLD.

BACKGROUND ART

The glucose content in blood is considered an important marker for diabetes. A diagnosis of diabetes is made by a simplified measurement (Point-of-Care Testing: POCT) such as a simplified test conducted by clinical staff or the like, or a self-inspection conducted by a patient, in addition to a clinical examination conducted in a hospital examination room or the like.

Although the simplified measurement is conducted using a glucose diagnostic kit or a measurement apparatus such as a biosensor or the like (POCT apparatus), a glucose oxidase is conventionally used in the POCT apparatus. However, the glucose oxidase depends on dissolved oxygen concentration, and thereby errors occur in measured values. Accordingly, use of glucose dehydrogenase which is not influenced by oxygen is recommended.

There are, as the glucose dehydrogenase, NAD coenzyme-unlinked glucose dehydrogenases of which the coenzyme is nicotinamide adenine dinucleotide (NAD) or nicotinamide adenine dinucleotide phosphate (NADP) and coenzyme-linked glucose dehydrogenases of which the coenzyme is pyrroloquinoline quinone (PQQ), flavin adenine dinucleotide (FAD), or the like. Among them, the coenzyme-linked glucose dehydrogenases are advantageous in that they are less liable to be affected by contamination components in comparison with the NAD coenzyme-unlinked glucose dehydrogenases, and they realize high measurement sensitivity and production of the POCT apparatuses at low cost.

However, conventional pyrroloquinoline quinone (PQQ)-type glucose dehydrogenases are disadvantageous in that the stability thereof is low, and they easily react with maltose or galactose. Maltose is a sugar used in a transfusion. When the PQQ-type glucose dehydrogenases react with maltose, the POCT apparatus which measures blood sugar levels indicates a higher blood sugar level than an actual blood sugar level. As a result, the patient injects an excessive amount of insulin, and thereby suffers from hypoglycaemia, which causes consciousness disorder or a comatose state, which has attracted tremendous interest.

In particular, the blood sugar POCT apparatus is used to measure the blood sugar level and the importance thereof has increased due to its convenience in patient self-care and medication, and thus self blood sugar monitoring apparatuses (Self-Monitoring of Blood Glucose: SMB) have been increasingly used in the home. Accordingly, the demand for realizing measurement accuracy is deemed to be very high.

In actuality, a notification calling for attention with respect to use of blood sugar testing apparatuses with an enzyme that utilizes PQQ as a coenzyme was issued to patients receiving maltose transfusion from the Japanese Ministry of Health, Labor and Welfare on February, 2005 (Feb. 7, 2005; Pharmaceutical and Food Safety Notification No. 0207005, and the like).

On the other hand, there have been reported, as the coenzyme-linked glucose dehydrogenases which catalyze dehydrogenation of glucose with FAD as the coenzyme, enzymes originating from Agrobacterium tumefaciens (J. Biol. Chem. (1967) 242: 3665-3672), enzymes originating from Cytophaga marinoflava (Appl. Biochem. Biotechnol. (1996) 56: 301-310), enzymes originating from Halomonas sp. α-15 (Enzyme Microb. Technol. (1998) 22: 269-274), enzymes originating from Agaricus bisporus (Arch. Microbiol. (1997) 167: 119-125, Appl. Microbiol. Biotechnol. (1999) 51: 58-64), and enzymes originating from Macrolepiota rhacodes (Arch. Microbiol. (2001) 176: 178-186). These enzymes oxidize a hydroxyl group at the 2-position and/or 3-position of glucose, and exhibit a high activity toward maltose, but low selectivity to glucose. Although coenzyme-linked glucose dehydrogenases originating from Burkhorderia cepacia with a high activity toward maltose are also known, their natural type enzyme is a heterooligomer enzyme composed of three subunits α, β, and γ, and known as a membrane-binding enzyme. Accordingly, there are disadvantages in that solubilization treatment is required to obtain the enzyme, and cloning of necessary subunits is simultaneously required to realize sufficient activity by cloning.

In the Society for Biotechnology, Japan (Oct. 28 to 30, 2002), there was a presentation regarding the substrate selectivity (activity against maltose and activity against galactose, with respect to the activity against glucose which is assumed to be 100%) in which SM4 strain exhibited 40% and 105%, JCM5506 strain exhibited 43% and 132%, JCM550 strain exhibited 57% and 123%, JCM2800 strain exhibited 83% and 108%, JCM2801 strain exhibited 74% and 117%, IFO14595 strain exhibited 38% and 104%, and IFO15124 strain exhibited 74% and 148%, and the presenter thereof stated that these strains exhibited high activity against maltose, which was disadvantageous if used for a self blood sugar monitoring apparatus, and therefore the presenter was going to improve the substrate selectivity by changing the sequence thereof.

In contrast, inventors of the present invention invented a novel soluble coenzyme-linked glucose dehydrogenase of which the coenzyme is FAD and which is not a membrane-bound type, and filed a patent application (Patent Document 1). The coenzyme-linked glucose dehydrogenase disclosed in Patent Document 1 oxidizes a hydroxyl group at the 1-position of glucose, is excellent in substrate-recognizing ability against glucose, is not influenced by dissolved oxygen, and exhibits low activity toward maltose (activity against maltose of 5% or less and activity against galactose of 5% or less, with respect to the activity against glucose which is assumed to be 100%), such excellent characteristics not being realized by conventional ones.

However, the coenzyme-linked glucose dehydrogenase disclosed in Patent Document 1 is isolated or extracted from liquid culture medium in which wild microorganisms (such as, for example, microorganisms belonging to the genus Aspergillus) are cultivated, and therefore, the production yield thereof is limited. In addition to the slight production yield of the enzyme, large amounts of sugar are bound to the enzyme, and therefore the enzyme is in a so-called "sugar-embedded-type enzyme" from which is coated by different kinds of sugar from N-type or O-type sugar chain which binds to general enzymes, as a result of which the activity thereof is difficult to be detected (that is, the enzyme activity is low), the sugar chain cannot be removed enzymatically or chemically, and thereby, the enzyme is scarcely stained by usual protein staining (using Coomassie Brilliant Blue G-250 or the like) after electrophoresis, and a terminal or internal amino acid sequence of the enzyme, which is necessary information for obtaining the gene, is difficult to decode by performing conventional purification. Accordingly, there is no case in which cloning of the enzyme gene succeeds to ascertain expression of the enzyme activity.

Although the existence of coenzyme-linked glucose dehydrogenases originating from *Aspergillus oryzae* was suggested in 1967 (Non-patent Document 1), only partial enzymatic properties thereof were revealed. Although the dehydrogenase was suggested to provide no influence on maltose, there are no detailed reports regarding the coenzyme-linked glucose dehydrogenases originating from *Aspergillus oryzae*, and no reports regarding coenzyme-linked glucose dehydrogenases originating from other microorganisms which oxidize a hydroxyl group at the 1-position of glucose, and also no reports regarding amino acid sequences or genes of the coenzyme-linked glucose dehydrogenases are known.

Although an idea of measuring glucose using a glucose dehydrogenase EC 1.1.99.10 is known (see Patent Document 15), there is no case in which any coenzyme-linked glucose dehydrogenases are produced to a practical level, and therefore, no coenzyme-linked glucose dehydrogenases have been developed for practical use in a sensor. The reason for this is the activity of the enzyme in the fungus body is weak, and even if the enzyme is secreted outside the fungus body, the amount thereof is extremely slight, and the activity thereof is weak because the enzyme is coated by a large amount of sugar, as a result of which the enzyme is difficult to detect. Accordingly, it is speculated that a gene of the enzyme can not be cloned.

It is been known that the measurement of glucose levels using a sensor utilizing a glucose oxidase is influenced by sugar chains of the enzyme, and thereby it is difficult for an enzyme originating from molds rich in sugar chains to be adapted to the glucose sensor (Non-patent Document 2). It is known, for example, that solid cultivation of microorganisms belonging to the genus *Aspergillus* increases the sugar content of yielded enzymes in comparison with liquid cultivation thereof (Non-patent Document 3), and thus it is known that solid cultivation generally increases sugar chains in comparison with liquid cultivation. Thus, one of reasons coenzyme-linked glucose dehydrogenases have not been developed for practical use until now is assumed to be because it has been difficult to reduce sugar chain contents of the glucose dehydrogenases originating from molds to utilize it in a glucose sensor even if cultivating conditions are investigated.

In fact, although the present inventors purified a coenzyme-linked glucose dehydrogenase originating from *Aspergillus terreus*, the inventors found that the obtained dehydrogenase was coated with a great amount of sugars to be in a form which may be called an "arabinogalactan embedded-type enzyme", as a result of which an enzyme-immobilized electrode formed by applying the enzyme on an electrode and then drying is not sufficiently dried, and the reactivity of a glucose sensor is deteriorated by the existence of the sugars.

Biogenetic methods in which gene stocks encoding proteins such as enzymes or the like are utilized to produce the proteins on a massive scale are known, and biogenetic methods for preparing glucose dehydrogenases as disclosed in Patent Documents 2 to 14 are known. These mainly relate to modification of PQQ glucose dehydrogenases, and provide modified PQQ glucose dehydrogenases, in which disadvantages of conventional PQQ glucose dehydrogenases, such as low substrate selectivity and low stability, are improved, and modified gene stocks for biogenetically preparing the modified PQQ glucose dehydrogenases.

[Patent Document 1] WO2004/058958 Pamphlet
[Patent Document 2] Japanese Laid-Open Patent Application No. 2000-312588
[Patent Document 3] Japanese Laid-Open Patent Application No. 2000-350588
[Patent Document 4] Japanese Laid-Open Patent Application No. 2000-354495
[Patent Document 5] Japanese Laid-Open Patent Application No. 2001-197888
[Patent Document 6] Japanese Laid-Open Patent Application No. 2001-346587
[Patent Document 7] Japanese Laid-Open Patent Application No. 2001-37483
[Patent Document 8] Japanese Laid-Open Patent Application No. 2004-173538
[Patent Document 9] Japanese Laid-Open Patent Application No. 2004-313172
[Patent Document 10] Japanese Laid-Open Patent Application No. 2004-313180
[Patent Document 11] Japanese Laid-Open Patent Application No. 2004-344145
[Patent Document 12] Japanese Unexamined Patent Application, First Publication No. H10-243786
[Patent Document 13] Published Japanese translation No. 2004-512047 of PCT International Publication
[Patent Document 14] WO2002/072839 Pamphlet
[Patent Document 15] Japanese Unexamined Patent Application, First Publication No. S59-25700
[Non-patent Document 1] Biochem. Biophys. Acta., 139, 277-293, 1967
[Non-patent Document 2] Appl Environ Microbiol., 64(4), 1405-1411, 1998
[Non-patent Document 3] Biosci. Biotechnol. Biochem., 62(10), 1938-1946, 1998

DISCLOSURE OF THE INVENTION

Problems to be Solved by the Invention

However, in the case of the modified PQQ glucose dehydrogenases prepared using the modified gene stocks, the degree of activity toward maltose is approximately 10% or more, which is high, with respect to the degree of activity toward glucose which is assumed to be 100%. When the reactivity toward maltose is lowered, the reactivity (specific activity) to glucose is also lowered. Accordingly, when the activity is monitored by an electrochemical measurement method under a condition in which the content of substrate is sufficient, functions as a glucose sensor are insufficiently exhibited, and practical application to POCT apparatuses or the like has not been realized.

Also, there are disadvantages that a coenzyme PQQ required for expressing activity of the PQQ glucose dehydrogenase is not produced by *Escherichia coli* bacterium which is broadly used as a recombinant host in general, and so the recombinant host thereof is limited to host microorganisms that produce PQQ (such as, for example, Pseudomonad).

The present invention has been achieved in view of the above-mentioned problems of the prior arts, and has as its object to provide: a coenzyme-linked glucose dehydrogenase, in which the problems caused by the great deal of sugar bonded to the enzyme are solved, and which has excellent characteristics such as an excellent reactivity toward glucose, thermal stability, and substrate-recognizing ability, and a low activity toward maltose; a method for easily producing the coenzyme-linked glucose dehydrogenase on a massive scale; a polynucleotide encoding the dehydrogenase; a method for producing the polynucleotide; a method for measuring glucose levels using the dehydrogenase; a reagent composition for measuring the glucose levels; and a biosensor for measuring the glucose levels.

Means for Solving the Problems

The inventors of the present invention considered that mass production of a glucose dehydrogenase that does not act on maltose needs to be realized at a practical cost by gene cloning, in addition to a decrease of the content of the sugar chain massively bonded to the dehydrogenase to an applicable level for measurement of glucose, so that the coenzyme-linked glucose dehydrogenase is broadly utilized for industrial application. Moreover, the inventors considered that decoding of terminal or internal amino acid sequences of the dehydrogenase and obtaining of information necessary for obtaining the gene are essential for cloning the gene, and therefore, removal of the great deal of sugar embedding the dehydrogenase, different from general N-type or O-type sugar chains, to improve the stainability of the protein as well as to realize HPLC analysis, is required. Accordingly, the inventors have earnestly investigated to obtain a purified dehydrogenase from which the sugar embedding the dehydrogenase is removed, the sugar making it difficult to perform protein staining and HPLC analysis. As a result, the inventors have found that solid cultivation enables the content of the sugar embedding the objective dehydrogenase to be reduced, and thereby the amino acid sequence thereof is revealed to obtain the gene thereof.

In order to solve the above-mentioned problems, the present invention provides a polynucleotide encoding a soluble coenzyme-linked glucose dehydrogenase (GLD) (hereinafter, may be referred to as "GLD polynucleotide"), characterized by catalyzing dehydrogenation of glucose in the presence of an electron acceptor and exhibiting 5% or less, preferably 3% or less, and more preferably 2% or less, of an activity toward maltose, with respect to an activity toward glucose.

In more detail, the polynucleotide is as follows.

(A) A GLD polynucleotide is characterized in that the GLD has the following properties 1) to 4) of:
1) utilizing flavin adenine dinucleotide (FAD) as a coenzyme;
2) having a subunit structure of a homodimer;
3) not utilizing oxygen as an electron acceptor; and
4) having an activity toward maltose of 5% or less, preferably 3% or less, and more preferably 2% or less, with respect to an activity toward glucose.

(B) Alternatively, a GLD polynucleotide is characterized in that the GLD has the following properties 1) to 3) of:
1) utilizing flavin adenine dinucleotide (FAD) as a coenzyme;
2) not utilizing oxygen as an electron acceptor; and
3) having an activity toward maltose of 5% or less, preferably 3% or less, and more preferably 2% or less, with respect to an activity toward glucose.

(C) Alternatively, a GLD polynucleotide is characterized in that the GLD has the following properties 1) to 4) of:
1) utilizing flavin adenine dinucleotide (FAD) as a coenzyme;
2) not utilizing oxygen as an electron acceptor;
3) having an activity toward maltose of 5% or less, preferably 3% or less, and more preferably 2% or less, with respect to an activity toward glucose; and
4) having a total sugar content (galactose, glucose, mannose, and arabinose) of 80 µg or less per µg of a protein.

(D) Alternatively, a GLD polynucleotide is characterized in that the GLD has the following properties 1) to 4) of:
1) utilizing flavin adenine dinucleotide (FAD) as a coenzyme;
2) not utilizing oxygen as an electron acceptor;
3) having an activity toward maltose of 5% or less, preferably 3% or less, and more preferably 2% or less, with respect to an activity toward glucose; and
4) having a total sugar content (galactose, glucose, mannose, arabinose) of 40 µg or less per unit of an enzyme activity;

(E) Alternatively, a polynucleotide encoding a coenzyme-linked glucose dehydrogenase includes at least one partial nucleotide sequence selected from consensus sequences of a nucleotide sequence encoding the coenzyme-linked glucose dehydrogenase, set forth in SEQ ID NOs. 5 to 7, the coenzyme-linked glucose dehydrogenase having the following properties a to d of:
a having a subunit molecular weight of approximately 63 kDa;
b utilizing FAD as a coenzyme;
c catalyzing a reaction in which a hydroxyl group at the 1-position of a glucose is oxidized and the glucose is converted to a glucono-δ-lactone; and
d having an activity toward maltose of 5% or less, with respect to an activity toward glucose.

In the above, the term "subunit molecular weight" set forth in the property a refers to a subunit molecular weight determined by subjecting a coenzyme-linked glucose dehydrogenase originating from prokaryotic cells in which the GLD polynucleotide with or without its signal peptide region is subjected to polyacrylamide gel electrophoresis (SDS-PAGE), the subunit molecular weight being within the range of 58 kDa to 63 kDa. When the subunit molecular weight is determined using a coenzyme-linked glucose dehydrogenase originating from eukaryotic cells, the subunit molecular weight is within the range of 58 kDa to 150 kDa.

(F) Alternatively, a polynucleotide encoding a coenzyme-linked glucose dehydrogenase includes at least one partial amino acid sequence selected from consensus sequences of the coenzyme-linked glucose dehydrogenase set forth in SEQ ID NOs. 8 to 12, the coenzyme-linked glucose dehydrogenase having the following properties a to d of:
a having a subunit molecular weight of approximately 63 kDa;
b utilizing a FAD as a coenzyme;
c catalyzing a reaction in which a hydroxyl group at the 1-position of a glucose is oxidized and the glucose is converted to a glucono-δ-lactone; and
d having an activity toward maltose of 5% or less with respect to an activity toward glucose.

In the above, the term "subunit molecular weight" set forth in the property a refers to a subunit molecular weight determined by subjecting a coenzyme-linked glucose dehydrogenase originating from prokaryotic cells in which the GLD polynucleotide with or without its signal peptide region is subjected to polyacrylamide gel electrophoresis (SDS-PAGE), the subunit molecular weight being within the range of 58 kDa to 63 kDa. When the subunit molecular weight is determined using a coenzyme-linked glucose dehydrogenase originating from eukaryotic cells, the subunit molecular weight is within the range of 58 kDa to 150 kDa.

The GLD encoded by the GLD polynucleotide is an enzyme that has physicochemical properties of catalyzing a reaction in which a hydroxyl group at the 1-position of glucose is oxidized in the presence of an electron acceptor with a flavin compound (flavin adenine dinucleotide) as a coenzyme. The GLD exhibits an activity toward maltose of 5% or less, preferably 3% or less, and more preferably 2% or less. The activity toward maltose is inhibited by 50% or more in the presence of 1,10-phenanthroline at a final concentration of 5 mM, preferably 2 mM, and more preferably 1 mM. Although the subunit structure of the GLD is a homodimer, there is a case in which a monomer thereof exhibits activity.

The total content of sugar (galactose, glucose, mannose, and arabinose) contained in the GLD encoded by the GLD polynucleotide is different from that of a wild type GLD, and is 80 µg or less, preferably 10 µg or less, more preferably 2 µg or less, and even more preferably 0.5 µg or less, per µg of protein.

Also, the total content of sugar (galactose, glucose, mannose, and arabinose) contained in the GLD encoded by the GLD polynucleotide is different from that of a wild type GLD, and is 40 µg or less, preferably 10 µg or less, more preferably 2 µg or less, and even more preferably 0.5 µg or less, per unit of enzyme activity.

The GLD encoded by the GLD polynucleotide has a subunit molecular weight of approximately 63 kDa, utilizes flavin adenine dinucleotide (FAD) as a coenzyme, catalyzes a reaction in which a hydroxyl group at the 1-position of glucose is oxidized and the glucose is converted to glucono-δ-lactone, and has an activity toward maltose of 5% or less with respect to activity toward glucose.

The GLD polynucleotide is specifically a polynucleotide isolated from a filamentous fungi or a basidiomycete, such as, for example, a microorganism belonging to the genus Aspergillus Penicillium, or the genus Ganoderma, and is particularly a polynucleotide isolated from Aspergillus terreus (A. terreus).

The specific aspect of the GLD polynucleotide according to the present invention is a polynucleotide containing a nucleotide sequence set forth in SEQ ID NO. 1 or a nucleotide sequence in which at least one base is deleted from, substituted in, or added to the nucleotide sequence set forth in SEQ ID NO. 1, and encoding the GLD having a glucose dehydration activity realized when a coenzyme, particularly FAD, is bonded thereto.

Also, the present invention provides a polynucleotide containing a nucleotide sequence with a homology of at least 60% to a polynucleotide composed of the nucleotide sequence set forth in SEQ ID NO. 1, and encoding the GLD having a glucose dehydration activity realized when a coenzyme, particularly FAD, is bonded thereto.

The term "nucleotide sequence with a homology of at least 60% to a polynucleotide composed of the nucleotide sequence set forth in SEQ ID NO. 1" refers to a nucleotide sequence of which the identity to the full-length nucleotide sequence set forth in SEQ ID NO. 1 is at least 60%, preferably at least 70%, more preferably at least 80%, even more preferably at least 90%, and particularly preferably at least 95%. The percentage of such a nucleotide sequence identity may be calculated using a published or commercially available software with an algorithm which conducts comparison using a base sequence (SEQ ID NO. 1 in the present invention) as a reference sequence. For example, BLAST, FASTA, or GENETYX (manufactured by Software Development Co., Ltd.) may be used, and these may be run with default parameters.

Also, the present invention provides a polynucleotide containing a nucleotide sequence which hybridizes under stringent conditions to a polynucleotide composed of a nucleotide sequence complementary to a polynucleotide composed of the nucleotide sequence set forth in SEQ ID NO. 1, and encoding the GLD having a glucose dehydration activity exhibited by binding a coenzyme, particularly FAD.

The first amino acid Met to the 19th amino acid Leu of the GLD encoded by the nucleotide sequence form a signal peptide thereof. A polynucleotide encoding this region may be suitably substituted or deleted depending on organisms or host vector systems.

Also, the present invention provides a method for producing the polynucleotide encoding the GLD, in which a microorganism having a GLD productivity is cultivated in a solid state, and the polynucleotide is cloned based on an information of the dehydrogenase produced. It is preferable that the microorganism used be at least one strain belonging to the genus Aspergillus, particularly Aspergillus terreus (A. terreus).

Moreover, the present invention provides the GLD encoded by any one of the above-mentioned polynucleotide nucleotide sequences. A more specific aspect of the GLD according to the present invention is a soluble GLD which catalyzes dehydrogenation of glucose in the presence of an electron acceptor, and has an activity toward maltose of 5% or less with respect to an activity toward glucose.

Also, the GLD has the following properties 1) to 4) of
1) utilizing flavin adenine dinucleotide as a coenzyme;
2) having a subunit structure of a homodimer;
3) not utilizing oxygen as an electron acceptor; and
4) having an activity toward maltose of 5% or less, preferably 3% or less, and more preferably 2% or less, with respect to an activity toward glucose.

Alternatively, the GLD has the following properties 1) to 3) of:
1) utilizing flavin adenine dinucleotide as a coenzyme;
2) not utilizing oxygen as an electron acceptor; and
3) having an activity toward maltose of 5% or less, preferably 3% or less, and more preferably 2% or less, with respect to an activity toward glucose.

Alternatively, the GLD has the following properties 1) to 4) of:
1) utilizing flavin adenine dinucleotide (FAD) as a coenzyme;
2) not utilizing oxygen as an electron acceptor;
3) having an activity toward maltose of 5% or less with respect to an activity toward glucose; and
4) having a total content of galactose, glucose, mannose, and arabinose, contained therein, of 80 µg or less per µg of a protein.

Alternatively, the GLD has the following properties 1) to 4) of:
1) utilizing flavin adenine dinucleotide (FAD) as a coenzyme;
2) not utilizing oxygen as an electron acceptor;
3) having an activity toward maltose of 5% or less with respect to an activity toward glucose; and
4) having a total content of galactose, glucose, mannose, and arabinose, contained therein, of 40 µg or less per unit of an enzyme activity.

Alternatively, the GLD has the following properties of:
a. having a subunit molecular weight of approximately 63 kDa;
b utilizing a FAD as a coenzyme;
c catalyzing a reaction in which a hydroxyl group at the 1-position of a glucose is oxidized and the glucose is converted to a glucono-δ-lactone; and
d having an activity toward maltose of 5% or less with respect to an activity toward glucose.

The GLD is isolated from filamentous fungi, preferably at least one strain belonging to the genus Aspergillus, and more preferably Aspergillus terreus.

A more specific aspect of the GLD according to the present invention is a GLD containing an amino acid sequence set forth in SEQ ID NO. 2, and which dehydrates glucose by binding to a coenzyme, particularly FAD. Also, a GLD containing an amino acid sequence in which at least one amino acid is deleted from, substituted in, or added to, the amino acid sequence set forth in SEQ ID NO. 2, and has a glucose dehydration activity exhibited by binding FAD is provided.

Also, the present invention provides a GLD containing an amino acid sequence with a sequence homology of at least 60% to the amino acid sequence set forth in SEQ ID NO. 2, and has a glucose dehydration activity exhibited by binding a coenzyme, particularly FAD. Although coenzyme-linked glucose dehydrogenases originating from drosophila have been conventionally known (Proc. Natl. Acad. Sci. 1983 October; 80: 6286-6288, "Biphasic expression and function of glucose dehydrogenase in Drosophila melanogaster."), the homology thereof to the amino acid sequence set forth in SEQ ID NO. 2 is 45 to 47%. Moreover, it is difficult for such a dehydrogenase originating from insects to be expressed in cells other than insect cells, and therefore the productivity thereof is very low. Accordingly, it is difficult for it to be industrially utilized. The dehydrogenase according to the present invention, containing an amino acid sequence with a sequence homology of at least 60% to the amino acid sequence set forth in SEQ ID NO. 2, can be expressed in an Escherichia coli bacterium or the like, and therefore, is easily utilized as an enzyme for industrial application.

Also, the present invention provides a polynucleotide encoding the GLD containing the amino acid sequence set forth in SEQ ID NO. 2.

The term "amino acid sequence with a sequence homology of at least 60% to the amino acid sequence set forth in SEQ ID NO. 2" refers to an amino acid sequence of which the identity to the full-length amino acid sequence set forth in SEQ ID NO. 2 is at least 60%, preferably at least 70%, more preferably at least 80%, even more preferably at least 90%, and particularly preferably at least 95%. The percentage of such an amino acid sequence identity may be calculated using a published or commercially available software with an algorithm which conducts comparison using a base sequence (SEQ ID NO. 2 in the present invention) as a reference sequence. For example, BLAST, FASTA, or GENETYX (manufactured by Software Development Co., Ltd.) may be used, and these may be run with default parameters.

Also, the present invention provides a method for producing the GLD, characterized in that a microorganism that produces any one of the above-mentioned GLDs is cultivated in a solid culture medium containing a wheat bran or an oatmeal to make the GLD produced in the cultivated product, and then the GLD is collected, and provides the GLD produced by the method.

Moreover, the present invention provides a recombinant vector carrying any one of the above-mentioned polynucleotides according to the present invention, a transformed cell prepared using the recombinant vector, a method for producing the GLD characterized in that the transformed cell is cultivated followed by collecting the GLD having a glucose dehydration activity from the cultivated product, and the GLD produced by the method.

To the GLD produced by such a method, no sugar chain is bonded. Even if the sugar chain is bonded to the GLD, it is generally an N-type or O-type sugar chain, and the bonding amount thereof is smaller than that of a wild type GLD. Also, the sugar chain is easily removed, and the GLD exhibits a high activity.

Also, the present invention provides a GLD containing an amino acid sequence set forth in amino acid 20 to amino acid 592 of SEQ ID NO. 2 or an amino acid sequence with a homology of at least 60% to the amino acid sequence, having a function equivalent to that of the above-mentioned GLD, and being produced by a peptide synthesis method or a gene recombinant method.

Moreover, the present invention provides a method for measuring glucose characterized by utilizing the above-mentioned GLD according to the present invention, a reagent composition for measuring glucose characterized by containing the above-mentioned GLD, and a biosensor for measuring glucose characterized by utilizing the above-mentioned GLD. In a preferable aspect of these, an electron acceptor, particularly ferricyanide, is utilized at a final concentration of within the range of 2 mM to 500 mM.

The term "polynucleotide" refers to a molecule in which at least 100 phosphoric esters of nucleosides in which purine or pyrimidine is connected to sugar with a β-N-glycosidic linkage, such as, ATP (adenosine triphosphate), GTP (guanosine triphosphate), CTP (cytidine triphosphate), UTP (uridine triphosphate); or dATP (deoxyadenosine triphosphate), dGTP (deoxyguanosine triphosphate), dCTP (deoxycytidine triphosphate), and dTTP (deoxythymidine triphosphate) are bonded. In more detail, the term "polynucleotide" includes genomic DNAs encoding the GLD, mRNAs trancripted from the genomic DNAs, cDNAs synthesized from the mRNAs, and polynucleotides obtained by PCR amplification using the mRNAs as templates. The term "oligonucleotide" refers to a molecule in which 2 to 99 nucleotides are linked together. The term "polypeptide" refers to a molecule composed of at least 30 amino acid residues binding together with an amide linkage (peptide linkage) or with a linkage of unnatural residues, and further includes ones to which sugar chains are added, and ones in which chemical modification is artificially conducted.

Other terms in this specification or concepts of the present invention will be circumstantially explained in the section of BEST MODE FOR CARRYING OUT THE INVENTION and EXAMPLES. Also, various techniques used for carrying out this invention are easily and reliably performed by those skilled in the art based on known documents or the like excepting techniques of which citations are indicated. For example, genetic engineering and molecular biological techniques can be performed in accordance with methods disclosed in Sambrook and Maniatis, in Molecular Cloning—A Laboratory Manual, Cold Spring Harbor Laboratory Press, New York, 1989; Ausubel, F. M. et al., Current Protocols in Molecular Biology, John Wiley & Sons, New York, N.Y., 1995, or the like, methods disclosed in documents cited therein, substantially equivalent methods, modified methods, or the like. The terms used in this specification are mainly based on IUPAC-IUB Commission on Biochemical Nomenclature or conventionally used in the art.

Effects of the Invention

The enzyme according to the present invention is a coenzyme-linked glucose dehydrogenase (GLD) of which the sugar content is reduced to the level that enables the GLD to be applied to a glucose sensor, the sugar content contained in a natural enzyme being a great amount, the GLD having excellent properties in terms of substrate-recognizing ability against glucose and low activity toward maltose. Also, the method for producing the dehydrogenase according to the present invention can produce the dehydrogenase uniformly on a massive scale.

The sugar content of the GLD artificially produced in such a way, the sugar content being an issue of coenzyme-linked glucose dehydrogenases that dehydrate glucose by binding FAD, can be controlled in accordance with objects. Accordingly, it is possible to modify the activity toward sugar (such as glucose) contained in samples to measure the blood sugar by preparing a dehydrogenase of which the sugar content is decreased.

The GLD according to the present invention does not substantially affect maltose at the time of measuring of the blood sugar, and therefore, the GLD can be applied to a high-precision SMBG apparatus, and greatly contributes to self-care-medication of diabetes patients.

BRIEF DESCRIPTION OF DRAWINGS

FIG. 1 shows results of sugar chain staining performed after cutting sugar chains of dehydrogenases and then subjecting them to SDS-PAGE.

FIG. 2 shows results of CBB staining performed after cutting sugar chains of dehydrogenases and then subjecting them to SDS-PAGE.

BEST MODE FOR CARRYING OUT THE INVENTION

Figure 3:
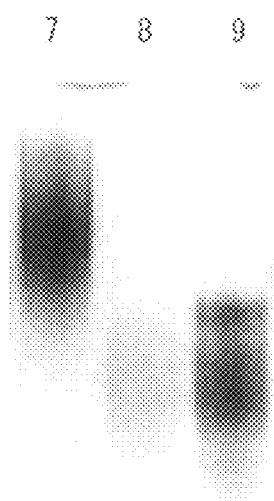
FIG. 3 shows results of activity staining performed after cutting sugar chains of dehydrogenases and then subjecting them to native-PAGE.

The GLD polynucleotide (gene) according to the present invention is a polynucleotide encoding a soluble GLD characterized by catalyzing oxidation of glucose in the presence of an electron acceptor, and having an activity toward maltose of 5% or less, preferably 3% or less, and more preferably 2% or less, with respect to an activity toward glucose. In more detail, the polynucleotide is the GLD polynucleotide characterized by having any one of the above-mentioned properties (A) to (F).

The most specific embodiment of the GLD polynucleotide according to the present invention is a polynucleotide containing a nucleotide sequence set forth in SEQ ID NO. 1. The polynucleotide is a GLD polynucleotide originating from a filamentous fungi, such as, for example, the genus *Aspergillus*, particularly *Aspergillus terreus* (FERM BP-08578), and encodes the GLD containing an amino acid sequence set forth in SEQ ID NO. 2.

The GLD polynucleotide may be obtained by preparing a cDNA library from *Aspergillus terreus* (FERM BP-08578), for example, and then determining the N-terminal or internal amino acid sequence of the GLD by Edman's method, followed by screening the cDNA library using plural oligonucleotide probes prepared based on the amino acid sequence.

A GLD collected from cultivated products obtained by cultivating at least one microorganism that can yield the GLD according to the present invention, such as, for example, at least one strain selected from the group consisting of *Aspergillus terreus*, *Aspergillus japonicus* (*A. japonicus*), and *Aspergillus oryzae* (*A. oryzae*), which belong to the genus *Aspergillus*, in a solid culture medium containing a wheat bran, oatmeal, or the like, has a low amount of sugar chains binding to the GLD, and therefore, can be easily purified by removing the sugar chains. Accordingly, it is preferable that the GLD obtained by solid cultivation be used to determine the N-terminal or internal sequence of the GLD.

When a wheat bran is used, a solution containing 40 to 70% by mass of the wheat bran is sterilized, 0.5 to 2% by mass of a seed culture liquid is added thereto, and cultivated at room temperature, followed by extracting a GLD crude enzyme from the obtained cultivated fungus body, for example. When an oatmeal is used, a solution containing 40 to 70% by mass of the oatmeal is sterilized, 0.5 to 2% by mass of a seed culture liquid is added thereto, and cultivated at room temperature, followed by extracting a GLD crude enzyme from the obtained cultivated fungus body, for example.

Although the probe may be labeled by a radioisotope (RI) method or non-radioisotope method, the probe is preferably labeled by the non-radioisotope method. As the non-radioisotope method, a fluorescent labeling method, biotin labeling method, chemiluminescence method, or the like may be adopted, and the fluorescent labeling method is preferably used. As the fluorescent substance, a substance which can bind to a base portion of an oligonucleotide may be suitably selected, and examples thereof include cyanine pigments (such as, for example, Cy3 and Cy5 of Cy Dye™ series), rhodamine 6G reagents, N-acetoxy-N2-acetylaminofluorene (AAF), AAIFs (iodide derivatives of AAF), and the like.

Alternatively, the objective GLD gene may be obtained by a PCR method in which the cDNA library derived from *Aspergillus terreus* (FERM BP-08578) is used as a template and a set of the oligonucleotide primer (probe) prepared in the above is used, or by a RT-PCR method in which a whole RNA or mRNA extracted from *Aspergillus terreus* (FERM BP-08578) is used as a template. The upstream region of the cDNA may be amplified by a 5'RACE-PCR method using a primer with an oligonucleotide sequence set forth in the 5' side of SEQ ID NO. 1, and the downstream region of the cDNA may be amplified by a 3'RACE-PCR method using a primer with an oligonucleotide sequence set forth in the 3' side of SEQ ID NO. 1. The primer is preferably designed to have a length (base number) of 15 to 40 bases, more preferably 15 to 30 bases, in order to satisfactorily realize specific annealing thereof to the template DNA. In the case where the primers are used for conducting a LA (long and accurate) PCR, the primers with a length of at least 30 bases are effectively used. A set or a pair (two) of a sense chain (5' terminal side) and an antisense chain (3' terminal side) is constructed so that both primers do not contain complementary sequences thereto for preventing both primers from annealing together. Moreover, GC content of the primers is set to be approximately 50% so as to prevent uneven distribution of GC-rich portions or AT-rich portions in the primers to realize stable binding. Since the annealing temperature depends on Tm (melting temperature), the primers whose Tm values are approximate to each other within the range of 55 to 65° C. are selected so as to obtain a PCR product with a high specificity. Also, it is to be noted that the final concentration of the primers used in PCR be within the range of approximately 0.1 to approximately 1 μM. A commercially available software for designing primers, such as, for example, Oligo™ (manufactured by National Bioscience Inc. (US)), or GENETYX (manufactured by Software Development Co., Ltd.) may be used.

The above-mentioned set of the oligonucleotide probe or oligonucleotide primer may be prepared by cutting the above-mentioned GLD cDNA using a suitable restriction enzyme, or by synthesizing in vitro by a well-known chemosynthesis technique as disclosed in documents (such as, for example, Carruthers (1982) Cold Spring Harbor Symp. Quant. Biol. 47: 411-418; Adams (1983) J. Am. Chem. Soc. 105: 661;

Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68: 90; Brown (1979) Meth. Enzymol. 68: 109; Beaucage (1981) Tetra. Lett. 22: 1859; U.S. Pat. No. 4,458,066).

The polynucleotide according to the present invention is composed of a nucleotide sequence with a homology of at least 60% to that set forth in SEQ ID NO. 1, and may encode the GLD that exhibits a glucose dehydration activity by binding to the coenzyme, particularly FAD.

The polynucleotide according to the present invention may have at least one base deleted from, substituted in, or added to the nucleotide sequence set forth in SEQ ID NO. 1, and may encode the GLD that realizes a glucose dehydration activity by binding to the coenzyme, particularly FAD.

The polynucleotide according to the present invention may have a capability of hybridization to DNA complementary to the nucleotide sequence set forth in SEQ ID NO. 1, or DNA with a nucleotide sequence complementary to that set forth in SEQ ID NO. 1, under stringent conditions, and also may encode the GLD that exhibits a glucose dehydration activity by binding to the coenzyme, particularly FAD.

The polynucleotide according to the present invention may have at least one partial nucleotide sequence selected from consensus sequences in the nucleotide sequence encoding the coenzyme-linked glucose dehydrogenase, set forth in SEQ ID NOs. 5 to 7. The polynucleotide according to the present invention may encode an enzyme having at least one partial amino acid sequence selected from consensus sequences in the coenzyme-linked glucose dehydrogenase, set forth in SEQ ID NOs. 8 to 12. The enzyme having such a consensus sequence (amino acid sequence) often exhibits an activity of the GLD according to the present invention, and therefore, such a portion is assumed to form an active center of the enzyme according to the present invention.

Regarding three characters "Xaa" in SEQ ID NO. 8, the first character "Xaa" represents amino acid "Ala" or "Gly", the second character "Xaa" represents amino acid "Ala" or "Val", and the third character "Xaa" represents "Ile" or "Val". Regarding four characters "Xaa" in SEQ ID NO. 9, the first character "Xaa" represents amino acid "Ala" or "Val", the second character "Xaa" represents amino acid "Ile" or "Leu", the third character "Xaa" represents amino acid "Ala" or "Ser", and the fourth character "Xaa" represents amino acid "Glu" or "Gln". Regarding three characters "Xaa" in SEQ ID NO. 10, the first character "Xaa" represents amino acid "Ala" or "Leu", the second character "Xaa" represents amino acid "Ile" or "Leu", and the third character "Xaa" represents amino acid "Ile" or "Val". Regarding three characters "Xaa" in SEQ ID NO. 12, the first character "Xaa" represents amino acid "Ala" or "Ser", the second character "Xaa" represents amino acid "Asn" or "Ser", and the third character "Xaa" represents amino acid "Ile" or "Val".

The polynucleotides encoding such an enzyme similar to GLD (GLD-like enzyme) may be prepared by modifying the above-mentioned GLD cDNA derived from *Aspergillus terreus* in accordance with a known mutation-introduction method, mutation-introduction PCR method, or the like. Alternatively, the polynucleotide may be obtained by a probe hybridization method using an oligonucleotide prepared based on an information of the nucleotide sequence set forth in SEQ ID NO. 1 from genomic DNAs of microorganisms other than *Aspergillus terreus* or cDNA libraries thereof. The polynucleotides encoding the GLD-like enzyme can be obtained by varying stringent conditions for hybridization. The stringent conditions are defined by salt concentration at a hybridization step and washing step, concentration of an organic solvent (formaldehyde or the like), temperature conditions, or the like, and various conditions known by a person skilled in the art, such as, for example, those disclosed in U.S. Pat. No. 6,100,037 or the like, may be adopted.

In more specific hybridization conditions, a filter is incubated at 42° C. with a mixture composed of 50% formamide, 5×SSC (150 mM sodium chloride, 15 mM trisodium citrate, 10 mM sodium phosphate, 1 mM ethylenediamine tetraacetic acid, pH 7.2), 5×Denhardt's solution, 0.1% SDS, 10% dextran sulfate, and 100 μg/mL of a modified salmon sperm DNA, and then washed at 42° C. with 0.2×SSC, for example.

The species or the genus of a microorganism used to obtain the polynucleotide encoding the GLD-like enzyme is not limited, and the microorganism may be a wild strain or a mutant strain. Examples thereof include a microorganism disclosed in Patent Document 1.

The recombinant vector according to the present invention is a cloning vector or an expression vector, and is suitably used in accordance with the kind of an insert polynucleotide and the application purpose thereof. For example, when the GLD or the GLD-like enzyme is produced using the cDNA or ORF region thereof as an insert, expression vectors for in vitro transcription, or expression vectors suitable to prokaryotic cells, such as, for example, *Escherichia coli* bacterium, or *Bacillus subtilis*, yeasts, filamentous fungi, such as, for example, molds, eukaryotic cells, such as, for example, insect cells, or mammalian cells, may be used.

When the GLD or the GLD-like enzyme is produced on a massive scale, the transformed cell according to the present invention may be prepared using a prokaryotic cell such as *Escherichia coli* bacterium, *Bacillus subtilis*, or the like, yeast, mold, eukaryotic cell, such as insect cells, mammalian cells, or the like, for example. The transformed cell may be prepared by introducing the recombinant vector into cells by a known method such as an electroporation method, calcium phosphate method, liposome method, DEAE dextran method, or the like. Specific examples of the recombinant vector include a recombinant vector pCGLD shown in the following example, and specific examples of the transformed cell include an *Escherichia coli* JM109/pCGLD (FERM BP-10243) prepared by transformation using the vector.

The GLD according to the present invention is a polypeptide having an amino acid sequence encoded by the above-mentioned GLD polynucleotide sequence. In more detail, it is preferable that the GLD be a soluble coenzyme-linked glucose dehydrogenase which catalyzes dehydrogenation of glucose in the presence of an electron acceptor, has an activity toward maltose of 5% or less with respect to an activity toward glucose, and further has any one of the above-mentioned properties (A) to (F).

In a more specific aspect of the GLD according to the present invention, the total content of sugars (galactose, glucose, mannose, and arabinose) contained therein is 80 μg or less per μg of a protein, or 40 μg or less per unit of an enzyme activity. The sugars form polysaccharides by polycondensation and envelope the enzyme. Accordingly, when the total content of the sugars contained therein is 80 μg or less per μg of a protein, or 40 μg or less per unit of an enzyme activity, the enzyme with a high activity can be obtained, and thus such a total content is preferable.

The more specific aspect of the GLD according to the present invention is composed of an amino acid sequence set forth in SEQ ID NO. 2. The GLD according to the present invention may also be a GLD-like enzyme composed of an amino acid sequence with a homology of at least 60% to that set forth in SEQ ID NO. 2, the GLD-like enzyme exhibiting a glucose dehydration activity by binding to a coenzyme, particularly FAD. The GLD according to the present invention may be a GLD-like enzyme composed of an amino acid sequence with at least one amino acid residue deleted from, substituted in, or added to the amino acid sequence set forth in SEQ ID NO. 2, the GLD-like enzyme exhibiting a glucose dehydration activity by binding to a coenzyme, particularly FAD. The GLD according to the present invention may be a polypeptide that has either an amino acid sequence set forth in amino acid 20 to amino acid 592 of SEQ ID NO. 2 or an amino acid sequence with a homology of at least 60% to the amino acid sequence, exhibits a function equivalent to that of the above-mentioned polypeptide, and is synthesized by a peptide synthesis method or gene recombinant method.

Such a GLD may be prepared, for example, based on the amino acid sequence set forth in SEQ ID NO. 2 or a similar sequence thereto by a known peptide synthesis method (Merrifield, R. B. J. Solid phase peptide synthesis I. The synthesis of tetrapeptide. J. Amer. Chem. Soc. 85, 2149-2154, 1963; Fmoc Solid Phase Peptide Synthesis. A Practical Approach. Chan, W. C. and White, P. D., Oxford University Press, 2000). The peptide may be formed by a residue linkage other than natural amide linkages. The residue linkage other than natural amide linkages may be formed by a chemical binding or coupling using glutaraldehyde, N-hydroxysuccinimide ester, bifunctional maleimide, N,N'-dicyclohexylcarbodiimide (DCC), N,N'-diisopropylcarbodiimide (DIC), or the like. Examples of a linkage group which can be substituted for a peptide binding include ketomethylene (for example, —C(=O)—CH$_2$— instead of —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, and ester (see, for example, Spatola (1983) in Chemistry and Biochemistry of Amino Acids, Peptides and Proteins, Vol. 7, pp 267-357, "Peptide Backbone Modifications" Marcell Dekker, NY).

The GLD may be obtained by a recombinant DNA technique using the above-mentioned GLD polynucleotide (cDNA or the coding region thereof). For example, RNA is prepared by in vitro transcription using a vector containing the above-mentioned polynucleotide, followed by subjecting the RNA as a template to in vitro translation to produce the GLD in vitro. When the polynucleotide is inserted into a suitable expression vector by a known-method, the GLD encoded by the polynucleotide can be yielded on a massive scale using prokaryotic cells such as *Escherichia coli* bacterium, *Bacillus subtilis*, or the like, yeasts, molds, eukaryotic cells such as insect cells, mammalian cells, or the like. A host to be used is suitably selected in accordance with necessity or not of sugar chains, and necessity of other peptide modification.

In order to produce the GLD in vitro, a recombinant vector is prepared by inserting the above-mentioned polynucleotide into a vector containing a promoter to which RNA polymerase can be bonded, followed by adding the vector to an in vitro translation system such as rabbit blood reticulocyte lysate or wheat germ extract, which contain RNA polymerase responding to the promoter. Examples of the promoter to which RNA polymerase can be bonded include T3, T7, SP6, and the like. Examples of the vector containing such a promoter include pKA1, pCDM8, pT3/T718, pT7/319, pBluescript II, and the like.

In the case where the GLD is produced by expressing DNA thereof in a microorganism such as *Escherichia coli* bacterium or the like, the GLD can be produced on a massive scale in the microorganism by preparing a recombinant expression vector in which the above-mentioned polynucleotide is inserted into an expression vector replicable in the microorganism, the expression vector having an origin, promoter, ribosome binding site, DNA cloning site, terminator sequence, and the like, followed by transforming host cells with the recombinant expression vector, and then cultivating the transformed cells. In this case, a GLD fraction containing an optional region can be obtained by adding an initiation codon and a stop codon in front of and behind a coding region of the optional region, followed by expressing the optional region. Alternatively, the GLD may be expressed as a protein fused with another protein. The fused protein may be cut with a suitable protease to obtain an objective GLD. Examples of the expression vector used in an *Escherichia coli* bacterium include pUC vectors, pBluescript II, pET expression vectors, pGEX expression vectors, pCold expression vectors, and the like.

The GLD can be produced in a eukaryotic cell by preparing a recombinant vector in which the above-mentioned polynucleotide is inserted into an expression vector replicable in eukaryotic cells, the expression vector having a promoter, splicing region, polyA-addition site, and the like, followed by transforming the eukaryotic cells with the recombinant vector. The recombinant vector may be held in the cells in such a state as that of a plasmid or may be held by incorporating it in a chromosome. Examples of the expression vector include pKA1, pCDM8, pSVK3, pSVL, pBK-CMV, pBK-RSV, EBV vector, pRS, pYE82, and the like. When pIND/V5-His, pFLAG-CMV-2, pEGFP-N1, pEGFP-C1, or the like is used as the expression vector, FAD-GLD polypeptide can be expressed as a fused protein to which a tag, such as His-tag, FLAG-tag, GFP or the like, is added. Although mammalian culture cells, such as monkey kidney cells COS-7, Chinese hamster ovary cells CHO, or the like, budding yeasts, fission yeasts, molds, silkworm cells, *xenopus oocytes*, are generally used as the eukaryotic cells, any eukaryotic cells may be used provided that they can yield the GLD. In order to introduce the expression vector into the eukaryotic cell, a known method such as an electroporation method, calcium phosphate method, liposome method, DEAE dextran method, or the like, may be adopted.

After the GLD is yielded in prokaryotic cells or eukaryotic cells, the objective protein is purified following isolation from cultivated products (such as, for example, fungus body, or cultivated liquid or culture medium composition, containing the enzyme secreted outward of the fungus body) by combining known separation procedures. Examples of such procedures include a treatment using a denaturant such as urea or a surfactant, thermal treatment, pH treatment, sonication, enzymatic digestion, salting-out or solvent precipitation method, dialysis, centrifugation, ultrafiltration, gel filtration, SDS-PAGE, isoelectric focusing electrophoresis, ion-exchange chromatography, hydrophobic chromatography, reversed-phase chromatography, affinity chromatography (including a method in which a tag sequence is utilized and a method in which a polyclonal or monoclonal antibody that is specific to UKC1 is utilized).

The GLD according to the present invention, which is prepared by the above-mentioned method, has the following characteristics.

(1) Action: The GLD is an enzyme classified in class EC 1.1.99.10 by International Union of Biochemistry (IUB) and catalyzes reaction in which a hydroxyl group at the 1-position of glucose is oxidized in the presence of an electron acceptor to produce glucono-δ-lactone (glucose+electron acceptor→glucono-δ-lactone+reduced-form electron acceptor).

Examples of the electron acceptor for use include phenazinemethosulfate, 1-methoxy-5-methylphenazium methylsulfate, 2,6-dichlorophenolindophenol, ferricyanide compounds, osmium compounds, quinone compounds, and the like.

(2) Substrate selectivity: The GLD strongly acts on D-glucose, but weakly acts on D-mannose, 1,5-anhydro-D-glucitol, D-cellobiose, D-trehalose, maltose, D-galactose, D-glucose-6-phosphate, and D-fructose. The GLD exhibits almost no action on L-arabinose, lactose, D-sorbitol, gluconic acid, sucrose, D-mannitol, L-sorbose, D-ribose, L-rhamnose, D-glucose-1-phosphate, D-raffinose, ethanol, and glycerol.

(3) Inhibitor: At least 60% of the activity is inhibited by 1,10-phenanthroline.

(4) Coenzyme: Flavin adenine dinucleotide (5) Optimum pH: 7.0 to 9.0

(6) Stable pH: 4.5 to 8.5

(7) Optimum temperature: approximately 55° C.

(8) Temperature stability: The GLD is stable at approximately 50° C. or lower.

Since sugar chains attach to the enzyme, the above-mentioned molecular weight thereof varies in accordance with cultivating conditions or purification conditions. In the case of the recombinant, the kind of sugar chain or amino acid attaching thereto varies in accordance with the kind of the host or vector used, and therefore, the molecular weight thereof also varies.

It is ascertained that the isoelectric focusing also varies in a similar manner to the above.

As described above, the GLD according to the present invention is an enzyme which catalyzes dehydrogenation of glucose in the presence of an electron acceptor, and therefore, the use thereof is not particularly limited, provided that it utilizes the change caused by the dehydrogenation. For example, the GLD may be used in medical fields or clinical fields for measuring glucose in samples containing biomaterials, or for composing a reagent for measuring glucose or a reagent for eliminating glucose. Alternatively, the GLD may be used for producing a substance using a coenzyme-linked glucose dehydrogenase.

The biosensor according to the present invention contains the GLD according to the present invention as an enzyme in a reaction layer, and is a glucose sensor for measuring glucose concentration in sample liquids. For example, the biosensor is prepared by forming an electrode system having a working pole, counter pole thereof, and reference pole, on an insulating base plate by a screen printing method or the like, followed by forming an enzyme reaction layer containing a hydrophilic polymer, oxidoreductase, and electron acceptor, onto the electrode system. When a sample liquid containing a substrate is dropped onto the enzyme reaction layer of the biosensor, the enzyme reaction layer is dissolved, and then the substrate is reacted with the enzyme, as a result of which the electron acceptor is reduced. After the enzyme reaction is ended, the reduced electron acceptor is electrochemically oxidized to measure the oxidation current value. The concentration of the substrate in the sample liquid is determined by the oxidation current value. In addition to the above, a biosensor that detects change of developed color or pH may be constructed.

As the electron acceptor of the biosensor, chemical substances that have an excellent electron donating and accepting ability may be used. The term "chemical substances that have an excellent electron donating and accepting ability" refer to chemical substances generally called an "electron carrier", "mediator" or "redox mediator", and examples thereof include electron carriers and redox mediators disclosed in Published Japanese translation No. 2002-526759 of PCT International Publication. Specific examples thereof include osmium compounds, quinone compounds, ferricyanide compounds, and the like.

As the electron acceptor of the biosensor, cheap potassium ferricyanide (potassium hexacyanoferrate (III)) is often used at the final concentration of 1 mM or less. However, D-glucose can be further sensitively measured by using potassium ferricyanide in a high concentration of 2 to 500 mM, and more preferably 30 to 100 mM. It is preferable that potassium ferricyanide be used at the final concentration of 2 to 500 mM in the measurement reaction system of the measurement method, reagent for measurement, compound for measurement, or biosensor, according to the present invention.

In measurement of the activity of the enzyme according to the present invention, it is preferable that the enzyme be suitably diluted to the final concentration of 0.1 to 1.0 unit/ml, for use. One unit of the enzyme activity is equivalent to the enzyme activity that oxidizes 1 μmol of glucose per minute. The enzyme activity of the coenzyme-linked glucose dehydrogenase according to the present invention may be determined in accordance with the following method.

(i) Enzyme Activity Measurement Method-1

1.0 ml of 0.1 M potassium phosphate buffer (pH 7.0), 1.0 ml of 1.0 M D-glucose, 0.1 ml of 3 mM 2,6-dichlorophenolindophenol (hereinafter, referred to as DCIP), 0.2 ml of 3 mM 1-methoxy-5-methylphenazium methylsulfate, and 0.65 ml of water are placed in a 3 ml quartz cell (with an optical path length of 1 cm), and then the cell is placed in a spectrophotometer equipped with a thermostat cell holder. After the cell is incubated at 37° C. for five minutes, 0.05 ml of an enzyme liquid is added thereto, followed by measuring absorbance change (ΔABS/min) of DCIP at 600 nm. The mol-absorption coefficient of DCIP at pH 7.0 is defined to be $16.3 \times 10^3$ $cm^{-1}M^{-1}$. Since one unit of the enzyme activity is substantially equivalent to the enzyme activity that reduces 1 μmol of DCIP per minute, the enzyme activity is determined by absorbance change in accordance with the following formula.

$$\text{Enzyme activity(unit/ml)} = \frac{-\Delta ABS}{16.3} \times \frac{3.0}{0.05} \times \text{dilution rate of enzyme}$$

(ii) Enzyme Activity Measurement Method-2

After 3.4 μl of 1.0 M potassium phosphate buffer (pH 7.0), 0.1 ml of 1.0 M D-glucose, and 86.6 μl of 20 mM DCIP are incubated at 37° C. for five minutes, 0.01 ml of an enzyme liquid is added thereto and then stirred to react the mixture for five minutes, followed by incubating the mixture for three minutes at 100° C. to stop the reaction. Moreover, 0.19 ml of 100 mM glycine/sodium buffer (pH 13.0) and 0.01 ml of 2.0 N potassium hydroxide are further added and incubated at 37° C. for ten minutes to convert D-gluconic acid in the mixture to D-glucono-δ-lactone, followed by adding 0.39 ml of 100 mM Tris-hydrochloride buffer (pH 7.5) and 0.01 ml of 1.0N hydrochloric acid thereto to obtain a neutral pH. The amount of D-gluconic acid in the mixture is quantitatively analyzed using a D-gluconic acid/D-glucono-δ-lactone quantitative analysis kit (manufactured by Roche Diagnostics K.K.). Since the enzyme activity that produces one μmol of D-glucono-δ-lactone per minute is substantially equivalent to one unit of the enzyme activity, the enzyme activity is determined based on the yield amount of D-glucono-δ-lactone.

In measurement of the protein concentration of the enzyme, the enzyme is preferably used by suitably diluting it to the final concentration of 0.2 to 0.9 mg/ml. The protein concentration may be determined by using a kit for measuring the protein concentration, purchased from Bio-Rad Laboratories, Inc., under the trade name of Bio-Rad Protein Assay, in accordance with an instruction manual, and calculating using a standard curve drawn by using bovine serum albumin (BSA, manufactured by Wako Pure Chemical Industries, Ltd., biochemical reagent) as a standard substance.

In the following, the present invention will be further circumstantially explained by showing some examples. However, the present invention is not limited to the following examples.

Example 1

1-1 (Seed Cultivation)

A pH of a liquid culture medium composed of 1% (W/V) glucose (manufactured by Wako Pure Chemical Industries, Ltd.), 2% (W/V) defatted soybean (manufactured by Nihon Syokuhan Co., Ltd.), 0.5% (W/V) corn steep liquor (manufactured by San-ei Sucrochemical Co., Ltd.), 0.1% (W/V) magnesium sulfate heptahydrate (manufactured by Nacalai Tesque, Inc.) and water was adjusted to 6.0. 100 mL of the liquid culture medium was placed in a Sakaguchi flask of 500 ml capacity, and plugged with cotton, followed by performing autoclave treatment at 121° C. for 20 minutes. After the culture medium was cooled, a strain of Aspergillus terreus (FERM BP-08578) was inoculated thereto, followed by cultivating while shaking at 28° C. for 48 hours to obtain a seed culture liquid.

1-2 (Obtaining Crude Enzyme Liquid by Liquid Cultivation)

A pH of 4 L of a liquid culture medium composed of 1% (W/V) glucose (manufactured by Wako Pure Chemical Industries, Ltd.), 2% (W/V) defatted soybean (manufactured by Nihon Syokuhan Co., Ltd.), 0.5% (W/V) corn steep liquor (manufactured by San-ei Sucrochemical Co., Ltd.), 0.1% (W/V) magnesium sulfate heptahydrate (manufactured by Nacalai Tesque, Inc.), an antifoamer, and water, was adjusted to 6.0. The liquid culture medium was placed in a jar fermenter of 5 L capacity, followed by performing autoclave treatment at 121° C. for 20 minutes to sterilize the liquid culture medium. After the liquid culture medium was cooled, 40 mL of the culture liquid disclosed in the above paragraph 1-1 (Seed cultivation) was seeded to the liquid culture medium, followed by cultivating fungus bodies for 41 hours under aerating and agitating conditions. The culture liquid was filtered to obtain a culture supernatant as a crude enzyme liquid 1.

1-3 (Obtaining Crude Enzyme Liquid by Solid Cultivation (Bran Cultivation))

300 g of wheat bran (manufactured by Yowa Seifun Co., Ltd.) and 240 g of tap water were put into a conical flask of 5 L capacity, and then stirred well. The conical flask was plugged with cotton, and then sterilized at 121° C. for 25 minutes.

5 mL of the seed culture liquid disclosed in the above-paragraph 1-1 (Seed cultivation) was seeded, and then left still at 26° C. for cultivation. After cultivation was performed for 2 weeks while occasionally stirring for aeration, cultivated fungus bodies attaching to the bran were subjected to extraction using 5 L of 20 mM potassium phosphate buffer (pH 7.5), and then filtration to obtain a supernatant as a crude enzyme liquid 2.

1-4 (Obtaining Crude Enzyme Liquid by Solid Cultivation (Oatmeal Cultivation))

300 g of oatmeal (manufactured by Snow Brand Milk Products Co., Ltd.) and 240 g of tap water were put into a conical flask of 5 L capacity, and then stirred well. The conical flask was plugged with cotton, and then sterilized at 121° C. for 25 minutes.

5 mL of the seed culture liquid disclosed in the above-paragraph 1-1 (Seed cultivation) was seeded, and then cultivated for four days at 25° C. by leaving it still while occasionally stirring for aeration. The cultivated fungus bodies attaching to the oatmeal were subjected to extraction using 5 L of 20 mM potassium phosphate buffer (pH 7.5), and then filtration to obtain a supernatant as a crude enzyme liquid 3.

1-5 (Purification of Enzyme)

The crude enzyme liquids 1 to 3 were subjected to enzyme purification by the following steps (1) to (5) to isolate the coenzyme-linked glucose dehydrogenase.

(1) Concentration and Desalination

Each crude enzyme liquid was concentrated using an ultrafiltration filter "Pellicon 2 modules" (manufactured by Millipore Corporation) with a molecular weight cutoff of 10,000, and then substituted with 20 mM potassium phosphate buffer (pH 7.5) to obtain each crude enzyme concentrate.

(2) Purification Using Butyl-TOYOPEARL650M (Manufactured by Tosoh Corporation) (First Time)

The above-mentioned crude enzyme concentrate was adjusted to be a 65% ammonium sulfate saturated solution (pH 7.5), and then centrifuged to obtain a supernatant. The crude enzyme supernatant was passed through a Butyl-TOYOPEARL650M column which was previously equilibrated with 20 mM potassium phosphate buffer (pH 7.5) containing 65% saturated ammonium sulfate so that the enzyme was adsorbed to the column. After the column was washed with the same buffer, the enzyme was eluted using 20 mM potassium phosphate buffer (pH 7.5) containing 30% saturated ammonium sulfate to collect an active fraction. Moreover, the enzyme was eluted by a gradient elution method using the same buffer to 20 mM potassium phosphate buffer (pH 7.5), and then mixed with the above-mentioned active fraction.

(3) Purification Using DEAE-CELLULOFINE A-500 (Manufactured by SEIKAGAKU CORPORATION)

The above-mentioned activity fraction was concentrated using an ultrafiltration filter "Pellicon 2 modules" with a molecular weight cutoff of 10,000, and then desalinated, followed by equilibrating with 15 mM Tris-hydrochloride buffer (pH 8.5). A DEAE-CELLULOFINE A-500 column was equilibrated with the same buffer, and the the fraction was passed through the column to collect an active fraction.

(4) Purification Using Butyl-TOYOPEARL650M (Manufactured by Tosoh Corporation) (Second Time)

The activity fraction was adjusted to be a 65% ammonium sulfate saturated solution (pH 7.5), and then centrifuged to obtain a supernatant. The supernatant was passed through a Butyl-TOYOPEARL650M column previously equilibrated with 20 mM potassium phosphate buffer (pH 7.5) containing 65% saturated ammonium sulfate so that the enzyme was adsorbed to the column. After the column was washed with the same buffer, the enzyme was eluted with 20 mM potassium phosphate buffer (pH 7.5) containing 30% saturated ammonium sulfate to collect an active fraction.

(5) Purification Using TSK-gel G3000SW (Manufactured by Tosoh Corporation)

The above-mentioned active fraction was concentrated with a pencil-type membrane concentration module "ACP-0013" with a molecular weight cutoff of 13,000 (manufactured by Asahi Kasei Corporation.), and then desalinated, followed by equilibrating with 50 mM potassium phosphate buffer (pH 5.5) containing 0.2 M sodium chloride. The fraction was passed through a TSK-gel G3000SW (with a diameter of 2.15 cm and a height of 60 cm) equilibrated with the same buffer, and then the enzyme was eluted with the same buffer to collect an active fraction. The active fraction was concentrated with CENTRIPLUS 10 (manufactured by Amicon Inc.), and then desalinated, followed by being substituted with 50 mM sodium citrate/phosphate buffer (pH 5.5). The specific activity of the enzyme purified from the crude enzyme liquid 1 (hereinafter, referred to as "purified enzyme 1") was approximately 1,800 units/mg. The specific activity of the enzyme purified from the crude enzyme liquid 2 (hereinafter, referred to as "purified enzyme 2") was approximately 1,010 units/mg. The specific activity of the enzyme purified from the crude enzyme liquid 3 (hereinafter, referred to as "purified enzyme 3") was equivalent to the above. The purification fold of each enzyme was 100-fold or more with respect to the crude enzyme liquid.

Example 2

(Preparation of Vector Containing Insert DNA)
(1) Isolation of Whole RNA 2 g of wet fungus bodies cultivated by the method described in the above paragraph 1-1 (Seed culture) of Example 1 were frozen with liquid nitrogen, and then 1.5 mg of whole RNA thereof was extracted using EASY Prep RNA (manufactured by TAKARA BIO INC.).
(2) Preparation of cDNA Library A cDNA library was prepared from the whole RNA by performing reverse transcription using a reverse transcriptase and oligo dT adaptor primer. As a regent, "3'-Full RACE Core Set" (manufactured by TAKARA BIO INC.) was used under conditions disclosed in the protocol of the operating manual thereof.
(3) Cloning of GLD Gene The GLD gene was amplified by PCR using the cDNA library as a template. As primers, plural oligonucleotides were synthesized based on the N-terminal and internal amino acid sequence of purified enzyme 2 free from embedding sugar, the amino acid sequence being determined by Edman's method, the purified enzyme 2 being obtained by purifying the crude enzyme liquid 2 in accordance with the method described in the above-paragraph 1-5 (purification of enzyme) of Example 1, and the crude enzyme liquid 2 being obtained by bran cultivation as described in the paragraph 1-3 (solid cultivation (bran cultivation)) of Example 1. Finally, a primer set of KpnF (SEQ ID NO. 3) and PstR (SEQ ID NO. 4) primers was used to obtain an objective GLD gene.

PCR was performed using a DNA polymerase and Pyrobest (manufactured by TAKARA BIO INC.) by performing 25 cycles of (94° C. for 30 seconds→55° C. for one minute→72° C. for two minutes).

Then, a pColdIII vector (manufactured by TAKARA BIO INC.) was cleaved with restriction enzymes PstI and KpnI, and then the PCR-amplified fraction treated with the same restriction enzymes was ligated to the vector, followed by being transfected to an Escherichia coli bacterium DH5α strain for transformation. Plasmid DNAs were prepared from 6 clones of obtained transformants, and then treated with the restriction enzymes PstI and KpnI, as a result of which each clone was conformed to have a fraction with an objective size. Among them, plasmids of 4 clones were prepared to determine the sequence of the insert contained therein, and each plasmid was confirmed to have an objective gene.

Example 3

(Transformation of Host and Purification of Enzyme)

A host Escherichia coli bacterium JM109 strain was transformed with the recombinant vector (pCGLD) prepared in Example 2, and transformant was selected on LB agar medium containing ampicillin. Then, the transformant was seeded in LB liquid culture medium containing 50 μg/ml of ampicillin, and then cultivated while shaking at 37° C. When the OD600 of the cultivated liquid reached approximately 0.4 to 0.5, the cultivated liquid was cooled to 15° C., and then left still for 30 minutes, followed by adding 1 mM IPTG thereto, and then further cultivating while shaking at 15° C. for 24 hours. After the cultivation was ended, the fungus bodies were collected by centrifugation, and then suspended with 10 mM potassium phosphate buffer (pH 7.5). After the fungus bodies were sonicated using a sonicator, a cell-free extract was obtained by centrifugation. It was confirmed by SDS-PAGE and activity measurement that an enzyme with an anticipated molecular weight was expressed. Also, it was confirmed that the enzyme activity was 0.09 U/mL of the cultivated liquid.

Moreover, the coenzyme-linked glucose dehydrogenase was isolated and purified by the following steps (1) to (5).
(1) Concentration The above-mentioned cell-free extract was concentrated with an ultrafiltration filter "Pellicon 2 modules" with a molecular weight cutoff of 10,000 (manufactured by Millipore Corporation), followed by substituting with 20 mM potassium phosphate buffer (pH 7.5) to obtain a crude enzyme liquid.
(2) Purification Using Butyl-TOYOPEARL650M (Manufactured by Tosoh Corporation) (First Time)

The above-mentioned crude enzyme liquid was adjusted to be a 65% ammonium sulfate saturated solution (pH7.5), followed by centrifuging to obtain a supernatant. The obtained crude enzyme supernatant was passed through a Butyl-TOYOPEARL650M column previously equilibrated with 20 mM potassium phosphate buffer (pH 7.5) containing 65% ammonium sulfate so that the enzyme was adsorbed. After the column was washed with the same buffer, the enzyme was eluted with 20 mM potassium phosphate buffer (pH 7.5) containing 30% ammonium sulfate to collect an active fraction. Furthermore, the enzyme was eluted by a gradient elution method using the same buffer to 20 mM potassium phosphate buffer (pH 7.5), and the collected active fraction was added to the above-mentioned active fraction.
(3) Purification Using DEAE-CELLULOFINE A-500 (Manufactured by SEIKAGAKU CORPORATION)

The above-mentioned active fraction was concentrated with an ultrafiltration filter "Pellicon 2 modules" with a molecular weight cutoff of 10,000, and then desalinated, followed by equilibrating with 15 mM Tris-hydrochloride buffer (pH8.5). The fraction was passed through a DEAE-CELLULOFINE A-500 column equilibrated with the same buffer to collect the eluant.
(4) Purification Using Butyl-TOYOPEARL650M (Manufactured by Tosoh Corporation) (Second Time)

The eluant was adjusted to be a 65% ammonium sulfate saturated solution (pH 7.5), and then centrifuged to obtain a supernatant. The supernatant was passed through a Butyl-TOYOPEARL650M column previously equilibrated with 20 mM potassium phosphate buffer (pH 7.5) containing 65% ammonium sulfate so that the enzyme was adsorbed. After the column was washed with the same buffer, the enzyme was eluted with 20 mM potassium phosphate buffer (pH 7.5) containing 30% ammonium sulfate to collect an active fraction.

(5) Purification Using TSK-gel G3000SW (Manufactured by Tosoh Corporation)

The above-mentioned active fraction was concentrated with a pencil-type membrane concentration module "ACP-0013" (manufactured by Asahi Kasei Corporation.) with a molecular weight cutoff of 13,000, and then desalinated, followed by equilibrating with 50 mM potassium phosphate buffer (pH 5.5) containing 0.2 M sodium chloride. The fraction was passed through TSK-gel G3000SW (with a diameter of 2.15 cm and a height of 60 cm) equilibrated with the same buffer, and then the enzyme was eluted with the same buffer to collect an active fraction. The active fraction was concentrated with CENTRIPLUS 10 (manufactured by Amicon Inc.), and then desalinated, followed by substituting with 50 mM sodium citrate/phosphate buffer (pH 5.5). The obtained enzyme (hereinafter, referred to as "purified enzyme 4") had a specific activity of approximately 2,450 units/mg and a purification fold of approximately 50-fold with respect to the crude enzyme liquid.

Example 4

(Transformation of Mold and Purification of Enzyme)

As a host, a strain of *A. oryzae* NS4 was used. As disclosed in Known Document 1 (Biosci. Biotech. Biochem., 61(8), 1367-1369, 1997), this strain was bred in 1997 (Heisei 9) at the National Research Institute of Brewing, has been used for analyzing transcription factors, culturing various strains with a high ability of yielding an enzyme, or the like, and has been commercially available.

A vector which can realize expression of the GLD gene was prepared using an improved amylase promoter derived from *A. oryzae* for gene expression in the strain as disclosed in Known Document 2 (Heterologous gene expression system in the genus *Aspergillus*, Toshitaka Minetoki, Chemistry & Biology, 38, 12, P831-838, 2000).

Transformation was performed basically in accordance with a method disclosed in Known Document 2 and Known Document 3 (Genetic engineering of *Aspergillus oryzae* for Japanese Sake, Masaya Gomi, Journal of the Brewing Society of Japan, pages 494 to 502, 2000). Selection of transformant with activity was repeatedly performed to obtain a strain of *Aspergillus oryzae* with an ability of yielding the GLD.

The strain was cultivated while shaking at 30° C. for 5 days in a liquid culture medium containing 1% peptone, 2% sucrose, 0.5% dipotassium hydrogen phosphate, and 0.05% magnesium sulfate to obtain a cultivated liquid with a GLD activity.

Purification was performed in accordance with the same method as that of Example 3, and then SDS polyacrylamide gel electrophoresis was performed to obtain an approximately single enzyme sample. The sample is referred to as "purified enzyme 5".

Example 5

(Transformation of Yeast and Purification of Enzyme)

A host used was a strain prepared by improving a strain of *Candida boidinii* S2 AOU-1, which is known as a yeast with a high ability of yielding protein, in accordance with a method disclosed in Known Document 4 (Laboratory Manual for Gene Expression, Production of useful protein in high expression system, edited by Isao Ishida and Tamie Ando, Kodansya Scientific Ltd., pages 100 to 129, 1994) for transfection of a heterologous gene. The strain of S2 AOU-1 was named as *Candida boidinii* SAM1958 and deposited in the National Institute of Bioscience and Human-Technology as Accession No. FERM BP-3766 on Feb. 25, 1992.

A vector which realizes expression of the GLD gene in the improved strain was prepared using a promoter induced by methanol, the promoter being derived from the strain of S2 AOU-1 as disclosed in Known Document 5 (Heterologous gene expression system by methanol-utilizing yeast, Hiroya Yurimoto and Yasuyoshi Sakai, Chemistry & Biology, 38, 8, P533-540, 2000). Then, transformants were selected in accordance with Known Documents 4 and 5 to obtain a strain of *Candida boidinii* with an ability of yielding the GLD.

The strain was cultivated while shaking at 28° C. for two days in a liquid culture medium containing 2% peptone, 1% yeast extract, 2% glycerol, and 1% methanol to obtain a cultivated liquid with a GLD activity.

Purification was performed in accordance with the same method as that of Example 3, and then SDS polyacrylamide gel electrophoresis was performed to obtain an approximately single enzyme sample. The sample is referred to as "purified enzyme 6".

Example 6

(Enzymatic Decomposition)

0.1% (v/v) SUMIZYME PX and 0.1% (v/v) SUMIZYME ARS were added to a portion of the crude enzyme liquid 1 prepared in paragraph 1-2 of Example 1 (obtaining crude enzyme liquid by liquid cultivation), and then reacted at 40° C. for two hours. After the reaction was ended, the reactant was subjected to SDS-PAGE, and then sugar chain staining using a sugar chain staining kit (Gelcode Glycoprotein Staining Kit (manufactured by PIERCE)) in accordance with a determined method. However, no decomposition of sugar chains could be recognized.

(Oxidation, Reduction, and Acid Hydrolysis by Metaperiodic Acid)

The crude enzyme liquid 1 was put into a 1.5 ml Eppendorf tube covered with aluminum foil in a protein amount of 20 μg, and then an eighth part of 0.8N sodium metaperiodate ($NaIO_4$) aqueous solution (final concentration thereof was 0.1N) was added thereto, followed by performing oxidation at 25° C. for 24 hours. Then, to the solution, a tenth part of 0.4N $NaBH_4$ aqueous solution was added, followed by performing reduction at room temperature for 10 hours. Furthermore, to this solution, a tenth part of 1N sulfuric acid aqueous solution was added, followed by performing hydrolysis at 25° C. for 24 hours. In the same manner as that of the above-mentioned enzymatic decomposition test, the reactant was subjected to SDS-PAGE and then sugar chain staining using a sugar chain staining kit. However, no decomposition of sugar chains could be recognized.

(Electrophoresis (Sugar Chain Staining, Coomassie Brilliant Blue (CBB) Staining, and Activity Staining))

To each enzyme liquid (purified enzymes 1, 2, 4, 5, and 6) prepared in Examples 1 to 5, one unit of glycopeptidase F (manufactured by Wako Pure Chemical Industries, Ltd.) was added per 0.1 mg of a protein therein, and then reacted at 37° C. for 15 hours to cut sugar chains, followed by subjecting to SDS-PAGE. The SDS-PAGE gel was subjected to sugar chain staining to confirm the amount of sugar chains and whether the sugar chains were cut. The sugar chain staining was performed using a sugar chain staining kit (Gelcode Glycoprotein Staining Kit (manufactured by PIERCE)) in accordance with a determined method (FIG. 1). As a result, existence of a great deal of sugar in the purified enzyme 1 prepared from the liquid cultivation supernatant was confirmed, and no difference between before and after treatment of cutting sugar chains was recognized, and therefore, it was assumed that the glycopeptidase F provided no influence thereon. On the other hand, it was confirmed that the molecular weights of the purified enzymes 2, 5, and 6, purified from the products cultivated in a solid state, decreased by cutting the sugar chains, and a portion of the sugar chains was cut with the glycopeptidase F.

Also, when SDS-PAGE and then Coomassie Brilliant Blue (CBB) staining were performed in the same way, the purified enzyme 1 was hardly stained with CBB, but the purified enzymes 2, 4, 5, and 6 were stained well with CBB (FIG. 2). As is apparent from the above results, the purified enzymes prepared by solid cultivation or gene recombination had a lower binding sugar content and were easily stained with CBB in comparison with the purified enzyme prepared by liquid cultivation.

Also, electrophoresis analysis was performed by native-PAGE using an electrophoresis gel of NPU-7.5L for native-PAGE (manufactured by ATTO CORPORATION), and then an activity staining was performed. Results thereof are shown in FIG. 3. Lane 7 indicates a result of a sample prepared by liquid cultivation, the enzyme activity thereof being adjusted to 20 mU. Lane 8 indicates a result of a sample prepared by bran cultivation, the enzyme activity thereof being adjusted to 20 mU. Lane 9 indicates a result of a sample prepared by oatmeal cultivation, the enzyme activity thereof being adjusted to 20 mU. Lane 7 indicates a result of the purified enzyme 1, lane 8 indicates a result of the purified enzyme 2, and lane 9 indicates a result of the purified enzyme 3.

The electrophoresis position of the purified enzymes 2 and 3, which are purified from the products cultivated in a solid state, was lower than that of the purified enzyme 1 purified from the supernatant cultivated in a liquid state. As is apparent from the above results, the sugar content in the obtained enzyme was decreased by changing the cultivation state from a liquid state to a solid state, and thereby, the obtained enzyme was easily stained with CBB.

In consideration of the results of the above examples, it was assumed that the purified enzyme 1 and the other purified enzymes differed in the sugar content and sugar composition, and so the sugar analysis of the enzymes was performed.

Example 7

(Analysis of Sugar Composition by ABME Labeling—HPLC Analysis)

First, 35 mg of methyl p-aminobenzoate (ABME) and 3.5 mg of sodium cyanoborohydride were put into a test tube, and then 350 µl of methanol and 41 µl of acetic acid were added, followed by stirring the mixture.

Each purified enzyme liquid prepared in the above-mentioned Examples 1 to 5 was adjusted to have a protein content of 1.0 mg/ml, and then 100 µl thereof was put into a test tube equipped with a screw cap, followed by drying up to harden under a nitrogen gas stream, adding 0.2 ml of 4N TFA (trifluoroacetic acid) solution thereto, and then reacting at 100° C. for 4 hours. After the reaction was ended, the reactant was dried up to harden under a reduced pressure in a tube evaporator, followed by adding 200 µl of ion-exchanged water thereto. Then, the drying-up procedure was repeated three times, and thus TFA was completely removed. In a fume hood, 200 µl of methanol, 20 µl of pyridine, and 20 µl of acetic acid anhydride were added to the resultant, and then left still at room temperature for two hours or longer to perform N-acetylation. The reactant liquid was dried up to harden under a nitrogen gas stream, and then dissolved in 1 ml of ion-exchanged water, followed by passing it through a cartridge column of PRE-SEP C18 (manufactured by Waters Corporation) previously washed, and then performing elution with 15 ml of ion-exchanged water. The eluant was concentrated under a reduced pressure using a rotary evaporator, and then transferred to a test tube equipped with a screw cap, followed by drying up to harden in a tube evaporator. The residue was dissolved in 20 µl of ion-exchanged water, and then 80 µl of the ABME reagent was added thereto, followed by reacting at 80° C. for 45 minutes. After the reaction was ended, the reactant liquid was dried up to harden under a nitrogen gas stream, followed by adding 2 ml of ion-exchanged water and 2 ml of diethyl ether thereto, and then stirring. The resultant was centrifuged and an ether layer containing unreacted ABME was removed. This ether extraction was repeated five times, and the obtained aqueous layer was dried up to harden in a tube evaporator to obtain a saccharide derivatized with ABME. This saccharide was dissolved in 2 ml of high-purity water to perform HPLC analysis.

A column used for HPLC analysis was Wakosil 5C18-200 (4.0×250 mm; manufactured by Wako Pure Chemical Industries, Ltd.), the column temperature was 40° C., the flowing rate was 0.5 mL/min, and solvents used were a mixture composed of 5% acetonitrile and 0.1M acetic acid solution (solvent A), and a mixture composed of 15% acetonitrile and 0.1M acetic acid solution (solvent B). Elution was performed in a solvent ratio A:B of 100:0 for 20 minutes after the sample was injected, and then elution was performed in such a linear solvent's concentration gradient manner that the solvent ratio A:B was changed to 0:100 over 80 minutes. UV detection wavelength was 304 nm.

As a result, galactose, mannose, arabinose, rhamnose, and N-acetylglucosamine were detected from the purified enzyme 1 derived from the product cultivated in a liquid state, but glucose was not detected therefrom. On the other hand, mannose and N-acetylglucosamine were detected from the purified enzyme 2 derived from the product cultivated with bran, but glucose, galactose, arabinose, and rhamnose were not detected therefrom. In addition, the sugar content of each purified enzyme is shown in Table 1.

TABLE 1

| | Sugar Content (µg) per Unit of Enzyme Activity | | | | | | |
|---|---|---|---|---|---|---|---|
| | Galactose | Glucose | Mannose | Arabinose | Xylose | Rhamnose | N-acetylglucosamine |
| Purified Enzyme 1 (derived from liquid-cultivated wild strain) | 11.9 | ND | 1.72 | 29.0 | ND | 1.72 | 0.434 |
| Purified Enzyme 2 (derived from bran-cultivated wild strain) | ND | ND | 0.269 | ND | ND | ND | 0.045 |
| Purified Enzyme 5 (derived from recombinant mold) | 0.046 | ND | 0.072 | ND | MD | ND | 0.015 |

TABLE 1-continued

| | Sugar Content (μg) per Unit of Enzyme Activity | | | | | | |
|---|---|---|---|---|---|---|---|
| | Galactose | Glucose | Mannose | Arabinose | Xylose | Rhamnose | N-acetylglucosamine |
| Purified Enzyme 6 (derived from recombinant yeast) | ND | 0.273 | 0.644 | ND | ND | ND | 0.023 |

Example 8

(Quality Examination of Coenzyme-Linked Glucose Dehydrogenase)

The purified enzymes 1 to 6, isolated in the above-mentioned Examples 1 to 5, were examined in terms of activity, substrate selectivity, inhibitor and coenzyme thereof. The enzyme activity was measured in accordance with methods disclosed as Enzyme activity measurement method-1 and Enzyme activity measurement method-2 on pages 36 and 37 of the specification of WO2004/058958.

1) Activity

Each purified enzyme was reacted with 500 mM D-glucose in the presence of 8.66 mM DCIP, and the resultant was subjected to quantitative analysis using a kit for D-gluconic acid/D-glucono-δ-lactone quantitative analysis (manufactured by Roche Diagnostics K.K.). As a result, it was confirmed that D-gluconic acid was produced in each purified enzyme, and thus it was revealed that the purified enzymes 2 to 6 were also enzymes which catalyze a reaction in which a hydroxyl group at the 1-position of D-glucose was oxidized in the same way as the purified enzyme 1.

2) Optimum pH:

The enzyme activity of the purified enzyme at various pH regions was measured in a similar way to Enzyme activity measurement method 2 except that a potassium phosphate buffer (pH 6.0 to 7.0), Tris-hydrochloride buffer (pH 7.4 to 8.0), or glycine-sodium hydroxide buffer (pH 8.6 to 9.1) (each buffer being used at the final concentration of 17 mM) was suitably used instead of a buffer used in the measurement method 2. As a result, the optimum pH of the purified enzymes 4, 5, and 6 was 7.0 to 9.0.

3) Stable pH

The purified enzyme was dissolved in 50 mM of each buffer, that is, acetic acid/sodium acetate buffer (pH 3.6 to 5.3), potassium phosphate buffer (pH 6.0 to 6.8), Tris-hydrochloride buffer (pH 7.7), or glycine-sodium hydroxide buffer (pH 8.6 to 10.0), and then held at 40° C. for 60 minutes, followed by measuring the enzyme activity in accordance with the activity measurement method-1 to analyze the residual rate of the enzyme activity. The stable pH of the purified enzyme 5 was 4.5 to 8.5.

4) Optimum Temperature

The coenzyme-linked glucose dehydrogenase was dissolved in 50 mM potassium phosphate buffer (pH 7.0), and then the enzyme activity in the temperature region between 30° C. and 62° C. was measured in accordance with the activity measurement method-1. As a result, the optimum temperature of the purified enzyme 5 was approximately 55° C.

5) Temperature Stability

The coenzyme-linked glucose dehydrogenase was dissolved in 50 mM potassium phosphate buffer (pH 7.0), and then held for 15 minutes at a temperature within the range of 0° C. to 55° C., followed by measuring the enzyme activity in accordance with the activity measurement method-1 to analyze the residual rate of the enzyme activity. The residual rate of the enzyme activity was calculated with respect to the enzyme activity exhibited when held at 0° C. for 15 minutes which is assumed to be 100%. As a result, 89% of the enzyme activity of the purified enzyme 5 was sustained even at 50° C., and the enzyme activity was stable at approximately 50° C. or lower.

6) Subunit Molecular Weight:

The purified enzyme was subjected to SDS-polyacrylamide gel electrophoresis (SDS-PAGE) using 12.5% polyacrylamide gel in accordance with a method disclosed by Laemmli et al., (Nature (1970) 227: 680-685). After the electrophoresis was ended, the gel was stained with Coomassie Brilliant Blue (CBB), and the mobility of the enzyme was compared with that of a molecular weight marker (LMW Marker; manufactured by Amersham Pharmacia Biotech, Inc.), as a result of which it was revealed that the subunit molecular weight of each enzyme was as follows: the subunit molecular weight of the purified enzyme 2 was approximately 71 kDa, that of the purified enzyme 4 was approximately 58 kDa, that of the purified enzyme 5 was approximately 81 kDa, and that of the purified enzyme 6 was approximately 128 kDa.

7) Substrate Selectivity

The enzyme activity of the purified enzymes 1 to 6 was measured in a similar way to the enzyme activity measurement method-1 except that D-glucose or each other substrate (each being used at the final concentration of 333 mM, excepting D-cellobiose being used at the final concentration of 193 mM, and D-trehalose and D-raffinose being used at the final concentration of 121 mM) was used instead of the substrate in the reaction liquid for measuring the activity by the activity measurement method-1. The activity against each substrate was calculated as a relative value with respect to the activity against D-glucose which is assumed to be 100%.

The enzyme activity was measured in a similar way to the above except that D-glucose was used at the final concentrations of 550 mM and 100 mM and maltose was used at the final concentrations of 550 mM and 100 mM, and then the relative activity (enzyme activity) thereof was determined. The activity toward maltose was calculated as a relative value with respect to the activity toward D-glucose.

In the same way as that of the purified enzyme 1, the purified enzymes 2 to 6 according to the present invention strongly acted on D-glucose, but wealdy acted on D-mannose, 1,5-anhydro-D-glucitol, D-cellobiose, D-trehalose, maltose, D-galactose, D-glucose-6-phosphate, and D-fructose. The purified enzymes 2 to 6 provided almost no action on L-arabinose, lactose, D-sorbitol, gluconic acid, sucrose, D-mannitol, L-sorbose, D-ribose, L-rhamnose, D-glucose-1-phosphate, D-raffinose, ethanol, and glycerol.

8) Inhibitor

To the reaction system in the activity measurement method-1, 1,10-phenanthroline dissolved in methanol so that each final concentration was 1 mM, 5 mM, 10 mM, 25 mM, or 50 mM, was added, followed by measuring the activity of the purified enzymes 1 to 6 by the activity measurement method-1. Each final concentration of methanol in the reaction system was 10% (v/v). As a control, methanol was added to the reaction system in the activity measurement method-1 at the final concentration of 10% (v/v), and then the activity was measured by the activity measurement method-1. As a result, each inhibition ratio realized by 1,10-phenanthroline formulated at the final concentration of 1 mM or more was 60% or more, which was high.

9) Coenzyme

D-glucose was added to the purified enzymes 1 to 6, and then absorption spectrometry was performed. In each case, the absorption maximums recognized at 385 nm and 465 nm disappeared by adding D-glucose, and thus it was revealed that a coenzyme thereof was FAD. The absorption maximums are specific to FAD, and cannot be recognized in a control reaction system in which only FAD is not contained.

Example 9

(Comparison of Sensor Characteristics)

Figure 4:
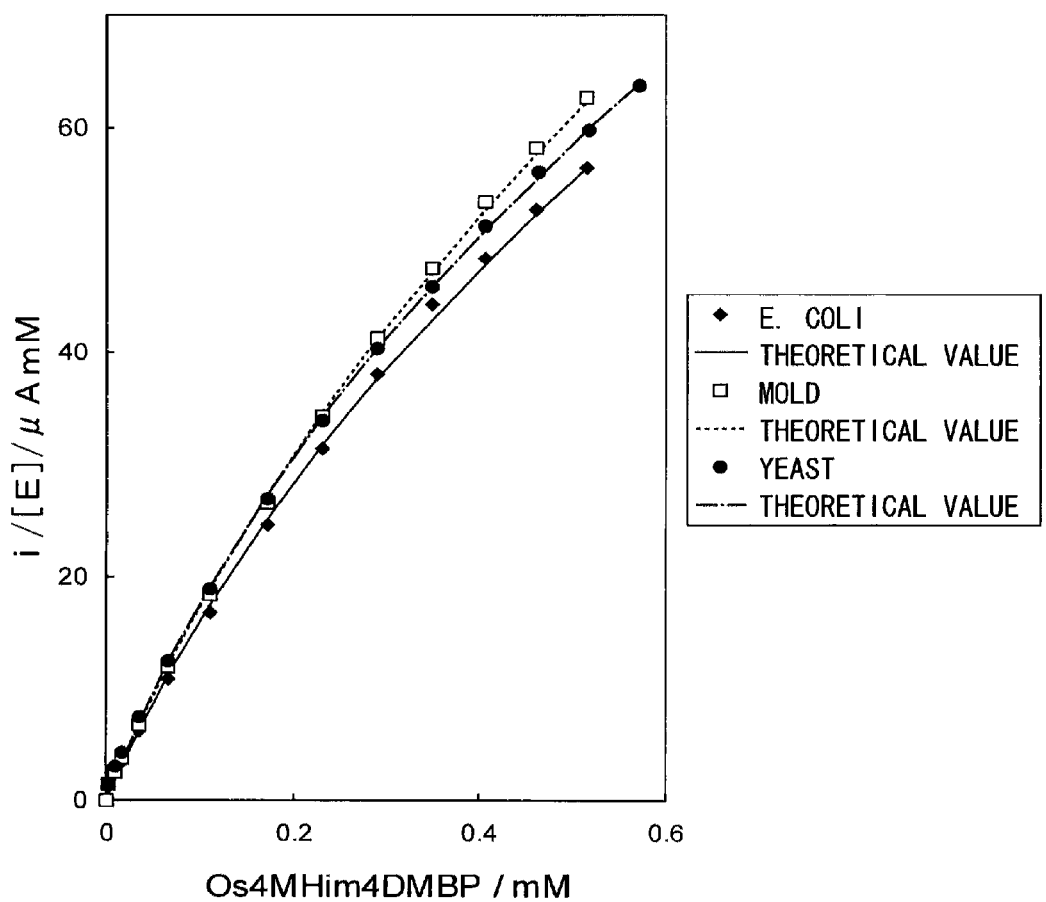
FIG. 4 shows results of measurement of sensor characteristics (bimolecular reaction rate constants) of dehydrogenases using an osmium complex as an electron acceptor.

Each bimolecular reaction rate constant of the purified enzyme 1 prepared in the paragraph 1-2 of Example 1 and the purified enzymes 4 to 6 prepared in Examples 3 to 5 was determined using an electrochemical analyzer of CHI611A (manufactured by BAS Inc.). A platinum auxiliary electrode, a carbon work electrode, and a silver/silver chloride reference electrode were used. To MOPS buffer with pH of 7.0, 142 mM of glucose, and any one of 0.45 µM of the purified enzyme 4, 0.76 µM of the purified enzyme 5, 1.9 µM of the purified enzyme 6, and 1.1 µM of the purified enzyme 1 were added, each concentration indicating the final concentration, followed by adding an osmium complex [Os(4-methyl-imidazole)$_2$(4-dimethyl-bipyridine)$_2$](PF$_6$)$_2$ at the final concentration of 0 mM to 0.57 mM, and then recording a cyclic voltammogram at each concentration (see FIG. 4). As a result, it was revealed that the bimolecular reaction rate constant of the purified enzyme 4 was $8.15 \times 10^4$ s$^{-1}$M$^{-1}$, the bimolecular reaction rate constant of the purified enzyme 5 was $7.36 \times 10^4$ s$^{-1}$M$^{-1}$, and the bimolecular reaction rate constant of the purified enzyme 6 was $9.38 \times 10^4$ s$^{-1}$M$^{-1}$. The purified enzyme 1 provided so low a current that the steady current value could not be found, and therefore, the bimolecular reaction rate constant could not be calculated (FIG. 4).

Figure 5:
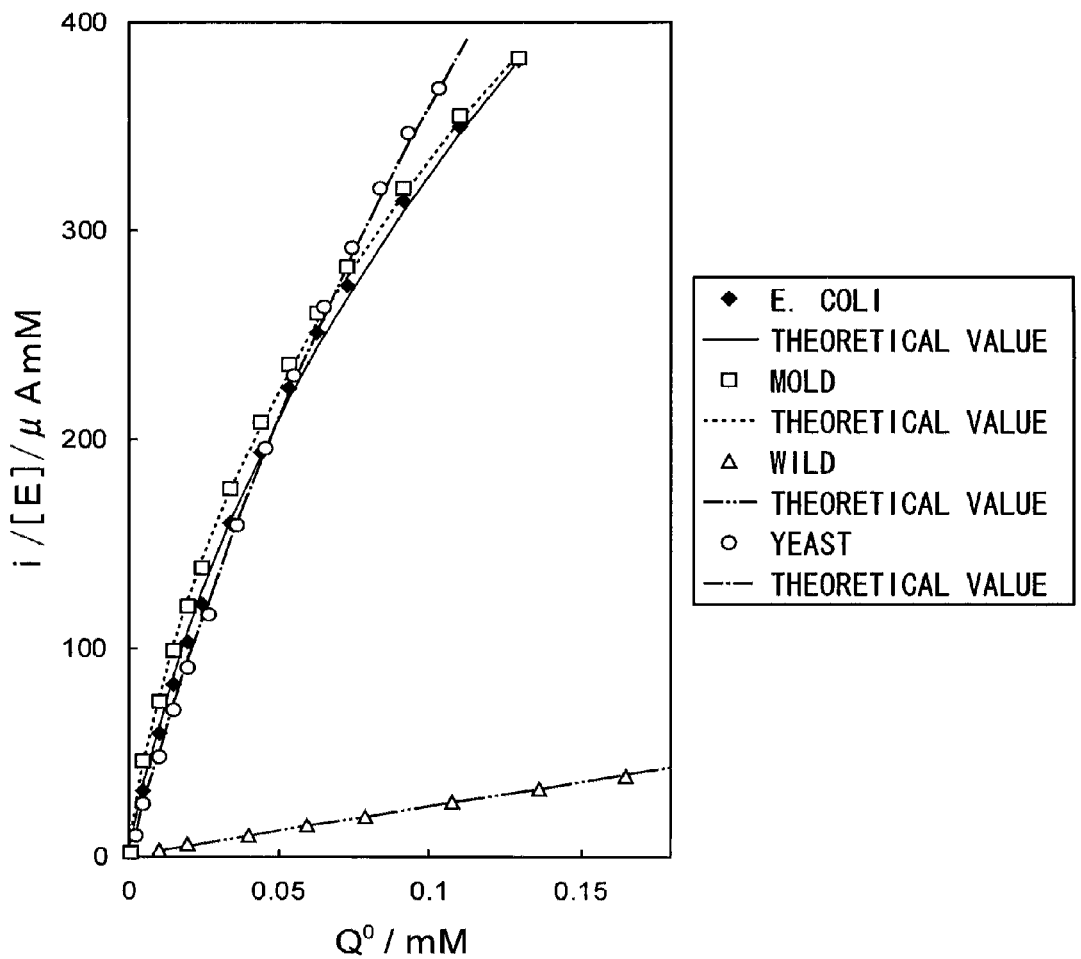
FIG. 5 shows results of measurement of sensor characteristics (bimolecular reaction rate constants) of dehydrogenases using a quinone compound as an electron acceptor.

In the same way, 142 mM of glucose, and any one of 0.45 µM of the purified enzyme 4, 0.76 µM of the purified enzyme 5, 0.55 µM of the purified enzyme 6, and 1.1 µM of the purified enzyme 1 were added to MOPS buffer with pH of 7.0, each concentration indicating the final concentration, followed by adding a quinone compound, 2,3-dimethoxy-5-methyl-1,4-benzoquinone, at the final concentration of 0 mM to 0.22 mM, and then recording cyclic voltammogram at each concentration (see FIG. 5). As a result, it was revealed that the bimolecular reaction rate constant of the purified enzyme 4 was $1.14 \times 10^8$ s$^{-1}$M$^{-1}$, the bimolecular reaction rate constant of the purified enzyme 5 was $5.29 \times 10^7$ s$^{-1}$M$^{-1}$, and the bimolecular reaction rate constant of the purified enzyme 6 was $2.49 \times 10^7$ s$^{-1}$M$^{-1}$. The purified enzyme 1 provided a low bimolecular reaction rate constant of $5.69 \times 10^4$ s$^{-1}$M$^{-1}$.

The results show that the enzymes derived from genetically engineered cells exhibited improved reactivity in comparison with the enzyme derived from a wild strain.

Each bimolecular reaction rate constant of the purified enzymes 1 and 2 prepared in the paragraphs 1-2 and 1-3 of Example 1 was determined using an electrochemical analyzer of CHI611A (manufactured by BAS Inc.). A platinum auxiliary electrode, a carbon work electrode, and a silver/silver chloride reference electrode were used. 142 mM of glucose and either 0.94 µM of the purified enzyme 1 or 3.3 µM of the purified enzyme 2 were added to MOPS buffer with pH of 7.0, each concentration indicating the final concentration, followed by adding potassium ferricyanide at the final concentration of 0 mM to 0.671 mM, and then recording a cyclic voltammogram at each potassium ferricyanide concentration (0, 0.019, 0.048, 0.095, 0.142, 0.188, 0.234, 0.280, 0.325, 0.370, 0.414, 0.458, 0.501, 0.544, 0.587, 0.629, and 0.671 mM). As a result, it was revealed that the bimolecular reaction rate constant of the purified enzyme 2 was $2.84 \times 10^3$ s$^{-1}$M$^{-1}$. The purified enzyme 1 provided so low a current that the steady current value could not be found, and therefore, the bimolecular reaction rate constant could not be calculated. It was assumed that the purified enzyme 1 exhibited low reactivity because it was a sugar-embedded type enzyme, while the purified enzyme 2 exhibited improved reactivity because it was an enzyme with normal sugar chains.

Example 10

(Measurement of Glucose Using Enzyme-Immobilized Electrode)

Figure 6:
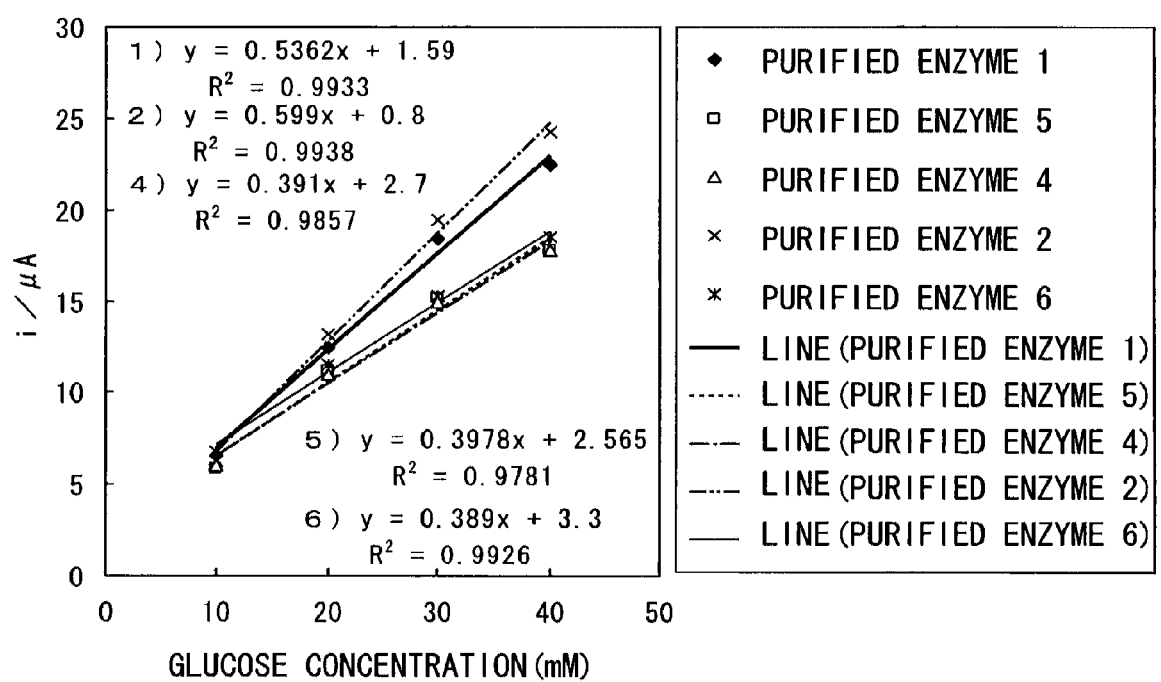
FIG. 6 shows results of quantitative analysis performed on D-glucose using enzyme-immobilized electrodes.

The concentration of D-glucose was measured by an enzyme-immobilized electrode using each purified enzymes 1, 2, 4, 5, and 6. The current value in response to the glucose concentration was measured using a glassy carbon (GC) electrode in which 1.0 U of each enzyme was immobilized. 1.8 ml of 50 mM sodium phosphate buffer (pH 7.0) and 0.2 ml of 1M potassium hexacyanoferrate (III) (potassium ferricyanide) aqueous solution were put into an electrolysis cell. After the GC electrode was connected to a potentiostat of BAS100B/W (manufactured by BAS), the solution was stirred at 40° C. and the voltage of +550 mV was applied to a silver/silver chloride reference electrode. To this system, 20 µl of 1M D-glucose solution was added and the current value at the steady-state was measured. In addition, the procedure in which the same amount of 1M D-glucose solution was added and then the current value was measured was repeated three times. The measured current values were plotted against the known glucose concentrations (approximately 10, 20, 30, and 40 mM) to generate each standard curve (FIG. 6). Thus, it was demonstrated that quantitative analysis of glucose can be realized by the enzyme-immobilized electrode using the GLD according to the present invention.

Example 11

Plural oligonucleotides were synthesized based on the sequence information set forth in SEQ ID NO. 1, and then oligonucleotides set forth in SEQ ID NO. 13 and SEQ ID NO. 14 were finally selected as a primer set. PCR was performed using the primer set and a template DNA derived from each strain with an ability of yielding the coenzyme-linked glucose dehydrogenase of which a coenzyme is FAD, that is, *Aspergillus japonicus* IFO4408, *Penicillium cyaneum* IFO5337, and *Ganoderma applanatum* IFO6498. The template DNA was prepared by cultivating each strain in accordance with the method described in Example 1 to obtain wet fungus bodies, freezing the wet fungus bodies with liquid nitrogen, crushing the fungus bodies, and then extracting with a mixture of phenol/chloroform/isoamyl alcohol (25:24:1) (manufactured by NIPPON GENE CO., LTD.). PCR was performed in 35 cycles of (94° C. for 30 seconds, 42° C. for 30 seconds, and then 72° C. for 1.5 minutes) using TaKaRa LA Taq (manufactured by TAKARA BIO INC.) and a thermal cycler (manufactured by Stratagene Corp.). Each sequence of amplified products with a length of approximately 1.6 kbp was analyzed. The cDNA sequence free from introns was compared with the sequence set forth in SEQ ID NO. 1 and sequences of a known glucose oxidase and sorbose dehydrogenase. As a result, it was revealed that nucleotide sequences (set forth in SEQ ID NOs. 5 to 7) and amino acid sequences (set forth in SEQ ID NOs. 8 to 12) are specific to the coenzyme-linked glucose dehydrogenase of which a coenzyme is FAD. In particular, it is assumed that the amino acid sequence set forth in SEQ ID NO. 8 is a binding site of FAD and is a portion of the active center.

INDUSTRIAL APPLICABILITY

The present invention can be utilized in a field of examination of diabetes.

The invention claimed is:

1. A cDNA encoding a coenzyme-linked glucose dehydrogenase, comprising the sequences set forth in SEQ ID NOs. 5 to 7, the coenzyme-linked glucose dehydrogenase having the following properties (a) to (d):
   (a) having a subunit molecular weight of approximately 63 kDa, wherein the term "subunit molecular weight" refers to a subunit molecular weight determined by subjecting a coenzyme-linked glucose dehydrogenase without sugar chains to polyacrylamide gel electrophoresis (SDS-PAGE);
   (b) utilizing a FAD as a coenzyme;
   (c) catalyzing a reaction in which a hydroxyl group at a 1-position of glucose is oxidized and the glucose is converted to glucono-δ-lactone; and
   (d) having an activity toward maltose of 5% or less with respect to an activity toward glucose.

2. A cDNA encoding a flavin adenine dinucleotide (FAD)-linked glucose dehydrogenase (GLD), the GLD comprising sequences set forth in SEQ ID NOs. 8 to 12, the coenzyme-linked glucose dehydrogenase having following properties (a) to (c):
   (a) having a subunit molecular weight of approximately 63 kDa, wherein the term "subunit molecular weight" refers to a subunit molecular weight determined by subjecting a coenzyme-linked glucose dehydrogenase without sugar chains polyacrylamide gel electrophoresis (SDS-PAGE);
   (b) catalyzing a reaction in which a hydroxyl group at a 1-position of glucose is oxidized and the glucose is converted to glucono-δ-lactone; and
   (c) having an activity toward maltose of 5% or less with respect to an activity toward glucose.

3. A cDNA encoding a flavin adenine dinucleotide (FAD)-linked glucose dehydrogenase (GLD) which catalyzes dehydrogenation of glucose in presence of an electron acceptor and having an activity toward maltose of 5% or less with respect to an activity toward glucose,
   wherein the GLD has an amino acid sequence with a homology of at least [[60%]] 90% to the amino acid sequence set forth in SEQ ID NO: 2 or the amino acid sequence set forth in amino acid 20 to 592 of SEQ ID NO: 2, and the cDNA is derived from an *Aspergillus terreus* (*A. terreus*).

4. A cDNA encoding a flavin adenine dinucleotide (FAD)-linked glucose dehydrogenase (GLD) which catalyzes dehydrogenation of glucose in presence of an electron acceptor and having an activity toward maltose of 5% or less with respect to an activity toward glucose, the cDNA comprising the nucleotide sequence set forth in SEQ ID NO. 1.

5. A vector comprising the cDNA set forth in claim 1.

6. An isolated transformed host cell comprising the vector set forth in claim 5.

7. A method for producing a coenzyme-linked glucose dehydrogenase, comprising culturing the isolated transformed host cell set forth in claim 6, thereby expressing the coenzyme-linked glucose dehydrogenase having a glucose dehydrogenation activity, and collecting the coenzyme-linked glucose dehydrogenase having a glucose dehydrogenation activity from the cultivated product.

8. A cDNA encoding a flavin adenine dinucleotide (FAD)-linked glucose dehydrogenase (GLD) which catalyzes dehydrogenation of glucose in presence of an electron acceptor and having an activity toward maltose of 5% or less with respect to an activity toward glucose,
wherein the GLD has an amino acid sequence with a homology of at least 90% to the amino acid sequence set forth in SEQ ID NO: 2 or the amino acid sequence set forth in amino acid 20 to 592 of SEQ ID NO: 2, the GLD is derived from a microorganism of an *Aspergillus* genus, *Penicillium* genus, or *Ganoderma* genus, and the GLD comprises at least one partial amino acid sequence selected from sequences of the coenzyme-linked glucose dehydrogenase set forth in SEQ ID NOs. 8 to 12.

9. A cDNA encoding a flavin adenine dinucleotide (FAD)-linked glucose dehydrogenase (GLD) catalyzing dehydrogenation of glucose in presence of an electron acceptor and having an activity toward maltose of 5% or less with respect to an activity toward glucose,
wherein the GLD has an amino acid sequence comprising sequences of the coenzyme-linked glucose dehydrogenase set forth in SEQ ID NOs. 8 to 12.

10. The cDNA of claim 1, wherein the cDNA is derived from an *Aspergillus terreus* (*A. terreus*).

11. The cDNA of claim 2, wherein the cDNA is derived from an *Aspergillus terreus* (*A. terreus*).

12. A vector comprising the cDNA set forth in claim 8.

13. A vector comprising the cDNA set forth in claim 9.

14. An isolated transformed host cell comprising the vector set forth in claim 12.

15. An isolated transformed host cell comprising the vector set forth in claim 13.

16. A method for producing a coenzyme-linked glucose dehydrogenase, comprising cultivating the isolated transformed host cell of claim 14, thereby expressing the coenzyme-linked glucose dehydrogenase having a glucose dehydrogenation activity, and collecting the coenzyme-linked glucose dehydrogenase having a glucose dehydrogenation activity from the cultivated product.

17. A method for producing a coenzyme-linked glucose dehydrogenase, comprising cultivating the isolated transformed host cell of claim 15, thereby expressing the coenzyme-linked glucose dehydrogenase having a glucose dehydrogenation activity, and collecting the coenzyme-linked glucose dehydrogenase having a glucose dehydrogenation activity from the cultivated product.

* * * * *

UNITED STATES PATENT AND TRADEMARK OFFICE
CERTIFICATE OF CORRECTION

PATENT NO. : 8,691,547 B2
APPLICATION NO. : 11/886885
DATED : April 8, 2014
INVENTOR(S) : Hironori Omura et al.

It is certified that error appears in the above-identified patent and that said Letters Patent is hereby corrected as shown below:

Claims

Claim 3, col. 42, line 67, "of at least [[60%]] 90% to the amino acid" should read -- of at least 90% to the amino acid --.

Claim 5, col. 43, line 11, "cDNA set forth in claim 1." should read -- cDNA set forth in claim 2. --.

Signed and Sealed this
Sixteenth Day of February, 2016

Michelle K. Lee
*Director of the United States Patent and Trademark Office*